United States Patent
Wilson et al.

(10) Patent No.: US 12,281,160 B2
(45) Date of Patent: Apr. 22, 2025

(54) METHOD OF TREATING ASTHMA

(71) Applicant: CSL LIMITED, Melbourne (AU)

(72) Inventors: Nicholas Wilson, Melbourne (AU); Steven Bozinovski, Melbourne (AU)

(73) Assignee: CSL LIMITED, Melbourne (AU)

( * ) Notice: Subject to any disclaimer, the term of this patent is extended or adjusted under 35 U.S.C. 154(b) by 1237 days.

(21) Appl. No.: 16/982,762

(22) PCT Filed: Mar. 22, 2019

(86) PCT No.: PCT/AU2019/050251
§ 371 (c)(1),
(2) Date: Sep. 21, 2020

(87) PCT Pub. No.: WO2019/178645
PCT Pub. Date: Sep. 26, 2019

(65) Prior Publication Data
US 2021/0009677 A1 Jan. 14, 2021

(30) Foreign Application Priority Data

Mar. 23, 2018 (AU) .............................. 2018900961

(51) Int. Cl.
*C07K 16/24* (2006.01)
*A61K 39/00* (2006.01)
*A61P 11/06* (2006.01)
*C07K 16/28* (2006.01)

(52) U.S. Cl.
CPC ............ *C07K 16/243* (2013.01); *A61P 11/06* (2018.01); *C07K 16/2866* (2013.01); *A61K 2039/505* (2013.01); *C07K 2317/34* (2013.01); *C07K 2317/565* (2013.01); *C07K 2317/622* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 4,196,265 A | 4/1980 | Koprowski et al. | |
| 4,676,980 A | 6/1987 | Segal et al. | |
| 4,816,567 A | 3/1989 | Cabilly et al. | |
| 5,225,539 A | 7/1993 | Winter | |
| 5,270,163 A | 12/1993 | Gold et al. | |
| 5,475,096 A | 12/1995 | Gold et al. | |
| 5,530,101 A | 6/1996 | Queen et al. | |
| 5,585,089 A | 12/1996 | Queen et al. | |
| 5,589,456 A | 12/1996 | Smith et al. | |
| 5,731,168 A | 3/1998 | Carter et al. | |
| 5,807,715 A | 9/1998 | Morrison et al. | |
| 5,885,793 A | 3/1999 | Griffiths et al. | |
| 6,248,516 B1 | 6/2001 | Winter et al. | |
| 6,300,064 B1 | 10/2001 | Knappik et al. | |
| 7,083,784 B2 | 8/2006 | Dall'Acqua et al. | |
| 7,108,852 B2 | 9/2006 | Devalaraja et al. | |
| 7,250,297 B1 | 7/2007 | Beste et al. | |
| 10,336,821 B2 | 7/2019 | Eriksson et al. | |
| 2004/0132028 A1 | 7/2004 | Stumpp et al. | |
| 2007/0135620 A1 | 6/2007 | Chamberlain et al. | |
| 2007/0224633 A1 | 9/2007 | Skerra et al. | |
| 2008/0139791 A1 | 6/2008 | Lipovsek et al. | |
| 2019/0119369 A1 | 4/2019 | Mehlem et al. | |

FOREIGN PATENT DOCUMENTS

| | | |
|---|---|---|
| CN | 107106681 A | 8/2017 |
| CN | 109310884 A | 2/2019 |
| EP | 0 569 141 A2 | 11/1993 |
| EP | 1167390 A1 | 1/2002 |
| WO | 94/04678 A1 | 3/1994 |
| WO | 94/07921 A1 | 4/1994 |
| WO | 1995021867 A1 | 8/1995 |
| WO | 97/49805 A2 | 12/1997 |
| WO | 98/44001 A1 | 10/1998 |
| WO | 99/32619 A1 | 7/1999 |
| WO | 99/45110 A1 | 9/1999 |
| WO | 99/49029 A1 | 9/1999 |
| WO | 99/53050 A1 | 10/1999 |
| WO | 99/57134 A1 | 11/1999 |
| WO | 00/34317 A2 | 6/2000 |
| WO | 01/34815 A1 | 5/2001 |
| WO | 02/080967 A1 | 10/2002 |
| WO | 02/088171 A2 | 11/2002 |
| WO | 02/098216 A1 | 12/2002 |
| WO | 2004/064724 A2 | 8/2004 |
| WO | 2004/108158 A1 | 12/2004 |

(Continued)

OTHER PUBLICATIONS

Sampson et al. Src kinases in G-CSF Receptor Signaling. Frontiers in Bioscience. 12: 1463-1474; Published: Jan. 1, 2007 (Year: 2007).*
Ashino et al. JAK1/3 signaling pathways are key initiators of TH2 differentiation and lung allergic responses. The Journal of Allergy and Clinical Immunology. 133(4): 1162-1174.e4; Published: Dec. 22, 2013 (Year: 2013).*
Tian et al. Multiple Signaling Pathways Induced by Granulocyte Colony-Stimulating Factor Involving Activation of JAKs, STATS, and/or STAT3 Are Required for Regulation of Three Distinct Classes of Immediate Early Genes. Blood. 88(12): 4435-4444; Published: Dec. 15, 1996 (Year: 1996).*
Hosoki et al. Analysis of a Panel of 48 Cytokines in BAL Fluids Specifically Identifies IL-8 Levels as the Only Cytokine that Distinguishes Controlled Asthma from Uncontrolled Asthma, and Correlates Inversely with FEV1. PLoS ONE. 10(5): e0126035; Published: May 26, 2015 (Year: 2015).*

(Continued)

*Primary Examiner* — Juliet C Switzer
*Assistant Examiner* — Katherine Ann Holtzman
(74) *Attorney, Agent, or Firm* — Scully, Scott, Murphy & Presser, P.C.

(57) ABSTRACT

The present disclosure relates to methods of treating asthma, such as allergic asthma, neutrophilic asthma, mixed granulocytic asthma, and severe asthma. The present disclosure also relates to compounds for use in the treatment of asthma, as well as the use of such compounds in the manufacture of medicaments for the treatment of asthma.

16 Claims, 7 Drawing Sheets
Specification includes a Sequence Listing.

(56) References Cited

FOREIGN PATENT DOCUMENTS

| | | |
|---|---|---|
| WO | 2005/056764 A2 | 6/2005 |
| WO | 2005/118629 A1 | 12/2005 |
| WO | 2006/033386 A1 | 3/2006 |
| WO | 2007025166 A2 | 3/2007 |
| WO | 2008003763 A1 | 1/2008 |
| WO | 2008017126 A1 | 2/2008 |
| WO | 2009039337 A2 | 3/2009 |
| WO | 2010/080538 A1 | 7/2010 |
| WO | 2010/085682 A2 | 7/2010 |
| WO | 2011/032204 A1 | 3/2011 |
| WO | 2011/051489 A2 | 5/2011 |
| WO | 2011/103076 A1 | 8/2011 |
| WO | 2011/107595 A1 | 9/2011 |
| WO | 2012/112188 A1 | 8/2012 |
| WO | WO 2012/017057 A1 | 12/2012 |
| WO | WO-2012171057 A1 * | 12/2012 ............. A61P 11/00 |
| WO | 2013/075066 A2 | 5/2013 |
| WO | 2014/072481 A1 | 5/2014 |
| WO | 2014/179657 A1 | 11/2014 |
| WO | 2015/063611 A2 | 5/2015 |
| WO | 2015/127405 A2 | 8/2015 |
| WO | WO 2015/0127405 A2 | 8/2015 |
| WO | 2019104385 A1 | 6/2019 |
| WO | 2019124666 A2 | 6/2019 |
| WO | 2019178645 A1 | 9/2019 |
| WO | 2020097139 A1 | 5/2020 |
| WO | 2020113270 A1 | 6/2020 |
| WO | 2020248024 A1 | 12/2020 |

OTHER PUBLICATIONS

Yalcin et al. IL-8, IL-10, Tgf-β, and GCSF LevelsWere Increased in Severe Persistent Allergic Asthma Patients with the Anti-IgE Treatment. Mediators of Inflammation. 2012: 720976; Published: Dec. 19, 2012 (Year: 2012).*

Liu et al. Mechanism of TH2/TH17-predominant and neutrophilic TH2/TH17-low subtypes of asthma. Journal of Allergy and Clinical Immunology. 139(5):1548-1558.e4; Published: May 3, 2017 (Year: 2017).*

Fahy and Dickey. Airway Mucus Function and Dysfunction. New England Journal of Medicine. 363: 2233-2247; Published: Dec. 2, 2010 (Year: 2010).*

Banuelos et al. Granulocyte colony-stimulating factor blockade enables dexamethasone to inhibit lipopolysaccharide-induced murine lung neutrophils. PloS ONE. 12(5): e0177884; Published: May 19, 2017 (Year: 2017).*

Carroll et al. Increased mast cells and neutrophils in submucosal mucous glands and mucus plugging in patients with asthma. Thorax. 57: 677-682; Published: Aug. 1, 2002 (Year: 2002).*

Manni et al. The complex relationship between inflammation and lung function in severe asthma. Mucosal Immunology. 7(5): 1186-1198; Published: Feb. 19, 2014 (Year: 2014).*

Wang et al. G-CSFR antagonism reduces neutrophilic inflammation during pneumococcal and influenza respiratory infections without compromising clearance. Scientific Reports. 9: 177732; Published: Nov. 27, 2019 (Year: 2019).*

Janeway et al. Immunobiology: The Immune System in Health and Disease. 5th edition. New York: Garland Science. The generation of diversity in immunoglobulins.; Published: 2001 (Year: 2001).*

Chiu and Gililand. Engineering antibody therapeutics. Current Opinion in Structural Biology. 38: 163-173; Published: Aug. 12, 2016 (Year: 2016).*

Chan et al. Therapeutic antibodies for autoimmunity and inflammation. Nature Reviews Immunology. 10(5):301-316; Published: May 2010 (Year: 2010).*

Wang et al. Anti G-CSFR Antibody Treatment Suppresses Neutrophilic and TYPE-2 Lung Inflammation in an Allergic Asthma Model Worsened By Neonatal Coinfection. Respirology. 23 (Supple 1): 21-103; Published: Mar. 14, 2018 (Year: 2018).*

International Search Report and Written Opinion dated May 21, 2019 issued in PCT/AU2019/050251.

Wang, H. et al., "Anti G-CSFR antibody treatment suppresses neutrophilic and type-2 lung inflammation in an allergic asthma model worsened by neonatal coinfection", Respirology (Mar. 14, 2018), vol. 23, Suppl. 1, pp. 21-103.

Yao, X. et al., "The A's have it: developing apolipoprotein A-I mimetic peptides into a novel treatment for asthma", Chest (2016), vol. 150, No. 2, pp. 283-288.

Scalzo-Inguanti, K. et al., "A neutralizing anti-G-CSFR antibody blocks G-CSF-induced neutrophilia without inducing neutropenia in nonhuman primates", Journal of Leukocyte Biology (Aug. 2017), vol. 102, pp. 537-549.

Toussaint, M. et al., "Host DNA released by NETosis promotes rhinovirus-induced type-2 allergic asthma exacerbation", Nature Medicine, Jun. 2017, pp. 681-691, vol. 23, No. 6.

Ueda, K. et al., "Granulocyte Colony Stimulating Factor Directly Inhibits Myocardial Ischemia-Reperfusion Injury Through Akt-EndotheHal No Synthase Pathway", Arterioscler Thromb Vasc Biol., 2006, pp. e108-e113, vol. 26.

Uhara, H. et al., "Neutrophilic dermatoses with acute myeloid leukemia associated with an increase of serum colony-stimulating factor", J Am Acad Dermatol, 2008, pp. S10-S12.

Wang, H. et al., "G-CSFR antagonism reduces neutrophilic inflammation during pneumococcal and influenza respiratory infections without compromising clearance", Scientific Reports, 2019, pp. 1-12, vol. 9, No. 17732.

Yan, J. et al., "Granulocyte Colony-Stimulating Factor Attenuates Renal Ischemia-Reperfusion Injury by Inducing Myeloid-Derived Suppressor Cells", JASN, 2020, pp. 731-746, vol. 31.

Zhang, Y. et al., "Ischemia-reperfusion induces G-CSF gene expression by renal medullary thick ascending limb cells in vivo and in vitro", Am J Physiol Renal Physiol, 2004, pp. F1193-F1201, vol. 286.

Aggarwal, A. et al., "G-CSF and IL-8 but not GM-CSF correlate with severity of pulmonary neutrophilia in acute respiratory distress syndrome", Eur Respir J, 2000, pp. 895-901, vol. 15.

Akihama, S. et al., "Bone Marrow-Derived Cells Mobilized by Granulocyte-Colony Stimulating Factor Facilitate Vascular Regeneration in Mouse Kidney after Ischemia/Reperfusion Injury", Tohoku J. Exp. Med., 2007, pp. 341-349, vol. 213.

ANZCTR, "Trial Review", 2016, pp. 1-6.

Ashchyan, A. et al., "Neutrophilic dermatoses: Pyoderma gangrenosum and other bowel- and arthritis-associated neutrophilic dermatoses", J AM ACAD Dermatol, Dec. 2018, pp. 1009-1022.

Banuelos, J. et al., "Granulocyte colony-stimulating factor blockade enables dexamethasone to inhibit lipopolysaccharide-induced murine lung neutrophils", PLOS One, 2017, pp. 1-16.

Bendele, A, "Animal models of rheumatoid arthritis", J Musculoskel Neuron Interact, 2001, pp. 377-385, vol. 1, No. 4.

Bidyasar, S. et al., "Sweet Syndrome Associated With Granulocyte Colony-Stimulating Factor", JCO, 2008, pp. 4355-4356.

Bostanci, M. et al., "The protective effect of G-CSF on experimental ischemia/ reperfusion injury in rat ovary", Arch Gynecol Obstet, 2016, pp. 789-795, vol. 293.

Bozinovski, S. et al., "Granulocyte/Macrophage-Colony-stimulating Factor (GM-CSF) Regulates Lung Innate Immunity to Lipopolysaccharide through Akt/Erk Activation of NFB and AP-1 in Vivo", The Journal of Biological Chemistry, 2002, pp. 42808-42814, vol. 277, No. 45.

Butler, D. et al., "What Do Autoinflammatory Syndromes Teach About Common Cutaneous Diseases Such as Pyoderma Gangrenosum? A Commentary", Dermatol Clin., 2013, pp. 427-435, vol. 31, No. 3.

Campbell, I. et al., "Therapeutic Targeting of the G-CSF Receptor Reduces Neutrophil Trafficking and Joint Inflammation in Antibody-Mediated Inflammatory Arthritis", J Immunol, 2016, pp. 1-11.

Cugno, M. et al., "Inflammatory Joint Disorders and Neutrophilic Dermatoses: a Comprehensive Review", Clinic Rev Allerg Immunol, 2018, pp. 269-281, vol. 54.

De La Lastra, J. et al., "Epitope mapping of 10 monoclonal antibodies against the pig analogue of human membrane cofactor protein (MCP)", Immunology, 1999, pp. 663-670, vol. 96.

(56) References Cited

OTHER PUBLICATIONS

DeVries, B. et al., "Complement Factor C5a Mediates Renal Ischemia-Reperfusion Injury Independent from Neutrophils", J Immunol, 2003, pp. 3883-3889, vol. 170.
DeBruin, C. et al., "Most purported antibodies to the human granulocyte colony-stimulating factor receptor are not specific", Experimental Hematology, 2010, pp. 1022-1035, vol. 38.
Dondelinger, M. et al., "Understanding the Significance and Implications of Antibody Numbering and Antigen-Binding Surface/Residue Definition", Front. Immunol., 2018, pp. 1-15, vol. 9.
Draper, B. et al., "Bullous Sweet's syndrome in congenital neutropenia: Association with pegfilgrastim", J AM ACAD Dermatol, May 2005, pp. 901-905, vol. 52, No. 5.
Elsasser, A. et al., "The fusion protein AML1-ETO in acute myeloid leukemia with translocation t(8;21)induces c-jun protein expression via the proximal AP-1 site of the c-jun promoter in an indirect, JNK-dependent manner", Oncogene, 2003, pp. 5646-5657, vol. 22.
Fujii, A. et al., "Sweet's Syndrome Successfully Treated with Granulocyte and Monocyte Adsorption Apheresis", Case Rep Dermatol, 2017,pp. 13-18, vol. 9.
Fukunaga, R. et al., "Three different mRNAs encoding human granulocyte colony-stimulating factor receptor", Proc. Natl. Acad. Sci. USA, Nov. 1990, pp. 8702-8706, vol. 87.
Goldberg, G. et al., "G-CSF and Neutrophils Are Nonredundant Mediators of Murine Experimental Autoimmune Uveoretinitis", The American Journal of Pathology, Jan. 2016, pp. 172-184, vol. 186, No. 1.
Guo, Y. et al., "The origin, transmission and clinical therapies on coronavirus disease 2019 (COVID-19) outbreak—an update on the status", Military Medical Research, 2020, pp. 1-10, vol. 7, No. 11.
Higuchi, T. et al., "Granulocyte Colony-Stimulating Factor Prevents Reperfusion Injury After Heart Preservation", Ann Thorac Surg., 2008, pp. 1367-1373, vol. 85.
Huang, C. et al., "Clinical features of patients infected with 2019 novel coronavirus in Wuhan, China", Lancet, 2020, pp. 497-506, vol. 395.
Jiang, H. et al., "Role for Granulocyte Colony Stimulating Factor in Angiotensin II-Induced Neutrophil Recruitment and Cardiac Fibrosis in Mice", American Journal of Hypertension, Oct. 2013, pp. 1224-1233, vol. 26, No. 10.
Kawakami, T. et al., "Elevated serum granulocyte colony-stimulating factor levels in patients with active phase of sweet syndrome and patients with active behcet disease: implication in neutrophil apoptosis dysfunction", Arch Dermatol, 2004, pp. 570-574, vol. 140, No. 5.
Ko, B. et al., "Affinity Maturation of Monoclonal Antibody 1E11 by Targeted Randomization in CDR3 Regions Optimizes Therapeutic Antibody Targeting of HER2-Positive Gastric Cancer", PLoS ONE, 2015, pp. 1-16, vol. 10, No. 7.
Layton, J. et al., "Neutralising Antibodies to the Granulocyte Colon••stimulating Factor Receptor Recognise both the Immunoglobulin-like Domain and the Cytokine Receptor Homologous Domain", Growth Factors, 1997, pp. 117-130, vol. 14.
Layton, J. et al., "Identification of a Ligand-binding Site on the Granulocyte Colony-stimulating Factor Receptor by Molecular Modeling", The Journal of Biological Chemistry, 1997, pp. 29795-29741, vol. 272, No. 47.
Layton, J. et al., "Interaction of Granulocyte Colony-stimulating Factor (G-CSF) with Its Receptor ", The Journal of Biological Chemistry, Jun. 1999, pp. 17445-17451, vol. 274, No. 25.
Layton, J. et al., "Identification of Ligand-binding Site III on the Immunoglobulin-like Domain of the Granulocyte Colony-stimulating Factor Receptor", The Journal of Biological Chemistry, Sep. 2001, pp. 36779-36787, vol. 276, No. 39.
Layton, J. et al., "The interaction of G-CSF with its receptor", Frontiers in Bioscience, Sep. 2006, pp. 3181-3189, vol. 11.
Lescure, F. et al., "Clinical and virological data of the first cases of COVID-19 in Europe: a case series", Lancet Infect Dis, 2020, pp. 1-10.
Li, Y. et al., "X-ray snapshots of the maturation of an antibody response to a protein antigen", Nature Structural Biology, Jun. 2003, pp. 482-488, vol. 10, No. 6.
Li, Y. et al., "Pretreatment with granulocyte colony-stimulating factor attenuated renal ischaemia and reperfusion injury via activation of PI3/Akt signal pathway", Nephrology, 2008, pp. 508-516, vol. 13.
Liao, J. et al., "Progress on role of cytokine storm in exacerbation of coronavirus disease 2019 (COVID-19): Review", Chinese journal of cellular and molecular immunology, 2020, pp. 941-947, vol. 36, No. 10.
Lloyd, C. et al., "Modelling the human immune response: performance of a 10 inch human antibody repertoire against a broad panel of therapeutically relevant antigens", Protein Engineering, Design & Selection, 2009, pp. 159-168, vol. 22, No. 3.
Lu, C. et al., "Neuroprotection of G-CSF in cerebral ischemia ", Frontiers in Bioscience, May 2007, pp. 2869-2875, vol. 12.
Navarini, A. et al., "Neutrophilic dermatoses and autoinflammatory diseases with skin involvement—innate immune disorders", Semin Immunopathol, 2016, pp. 45-56, vol. 38.
Nelson, C. et al., "Neutrophilic dermatoses: Pathogenesis, Sweet syndrome, neutrophilic eccrine hidradenitis, and Behcet disease", J AM ACAD Dermatol, Dec. 2018, pp. 987-1006.
Nishida, M et al., "How Does G-CSF Act on the Kidney during Acute Tubular Injury?", Nephron Exp Nephrol, 2006, pp. e123-e128, vol. 104.
Nogueira, B. et al., "Granulocyte Colony Stimulating Factor Prevents Kidney Infarction and Attenuates Renovascular Hypertension", Cell Physiol Biochem, 2012, pp. 143-152, vol. 29.
Prendiville, J. et al., "Neutrophilic Dermatoses in Two Children with Idiopathic Neutropenia: Association with Granulocyte Colony-Stimulating Factor (G-CSF) Therapy", Pediatric Dermatology, 2001, pp. 417-421, vol. 18, No. 5.
Qin, C. et al., "Dysregulation of immune response in patients with COVID-19 in Wuhan, China", Clin Infect Dis., 2020, pp. 1-24, vol. 71, No. 15.
Queto, T. et al., "G-CSF suppresses allergic pulmonary inflammation, downmodulating cytokine, chemokine and eosinophil production", Life Sciences, 2011, pp. 830-838, vol. 88.
Rajpal, A. et al., "A general method for greatly improving the affinity of antibodies by using combinatorial libraries", PNAS, 2005, pp. 8466-8471, vol. 102, No. 24.
Salvadori, M. et al., "Update on ischemia-reperfusion injury in kidney transplantation: Pathogenesis and treatment", World J Transplant, 2015, pp. 52-67, vol. 5, No. 2.
Shima, C. et al., "Neuroprotective Effects of Granulocyte Colony-Stimulating Factor on Ischemia-Reperfusion Injury of the Retina", Ophthalmic Res, 2012, pp. 199-207, vol. 48.
Steinberg, K. et al., "Evolution of Bronchoalveolar Cell Populations in the Adult Respiratory Distress Syndrome", American Journal of Respiratory and Critical Care Medicine, 1994, pp. 113-122.
Tian, S. et al., "Pulmonary Pathology of Early-Phase 2019 Novel Coronavirus (COVID-19) Pneumonia in Two Patients With Lung Cancer", Journal of Thoracic Oncology, 2020, pp. 700-704, vol. 15, No. 5.

\* cited by examiner

SEQUENCE LISTING

```
<160> NUMBER OF SEQ ID NOS: 18

<210> SEQ ID NO 1
<211> LENGTH: 319
<212> TYPE: PRT
<213> ORGANISM: artificial
<220> FEATURE:
<223> OTHER INFORMATION: amino acids 25-335 of Homo sapiens G-CSFR
      (hG-CSFR) with a C-terminal polyhistidine tag

<400> SEQUENCE: 1

Glu Cys Gly His Ile Ser Val Ser Ala Pro Ile Val His Leu Gly Asp
1               5                   10                  15

Pro Ile Thr Ala Ser Cys Ile Ile Lys Gln Asn Cys Ser His Leu Asp
            20                  25                  30

Pro Glu Pro Gln Ile Leu Trp Arg Leu Gly Ala Glu Leu Gln Pro Gly
        35                  40                  45

Gly Arg Gln Gln Arg Leu Ser Asp Gly Thr Gln Glu Ser Ile Ile Thr
    50                  55                  60

Leu Pro His Leu Asn His Thr Gln Ala Phe Leu Ser Cys Ala Leu Asn
65                  70                  75                  80

Trp Gly Asn Ser Leu Gln Ile Leu Asp Gln Val Glu Leu Arg Ala Gly
                85                  90                  95

Tyr Pro Pro Ala Ile Pro His Asn Leu Ser Cys Leu Met Asn Leu Thr
            100                 105                 110

Thr Ser Ser Leu Ile Cys Gln Trp Glu Pro Gly Pro Glu Thr His Leu
        115                 120                 125

Pro Thr Ser Phe Thr Leu Lys Ser Phe Lys Ser Arg Gly Asn Cys Gln
    130                 135                 140

Thr Gln Gly Asp Ser Ile Leu Asp Cys Val Pro Lys Asp Gly Gln Ser
145                 150                 155                 160

His Cys Ser Ile Pro Arg Lys His Leu Leu Leu Tyr Gln Asn Met Gly
                165                 170                 175

Ile Trp Val Gln Ala Glu Asn Ala Leu Gly Thr Ser Met Ser Pro Gln
            180                 185                 190

Leu Cys Leu Asp Pro Met Asp Val Val Lys Leu Glu Pro Pro Met Leu
        195                 200                 205

Arg Thr Met Asp Pro Ser Pro Glu Ala Ala Pro Pro Gln Ala Gly Cys
    210                 215                 220

Leu Gln Leu Ser Trp Glu Pro Trp Gln Pro Gly Leu His Ile Asn Gln
225                 230                 235                 240

Lys Cys Glu Leu Arg His Lys Pro Gln Arg Gly Glu Ala Ser Trp Ala
                245                 250                 255
```

```
Leu Val Gly Pro Leu Pro Leu Glu Ala Leu Gln Tyr Glu Leu Cys Gly
            260                 265                 270

Leu Leu Pro Ala Thr Ala Tyr Thr Leu Gln Ile Arg Cys Ile Arg Trp
        275                 280                 285

Pro Leu Pro Gly His Trp Ser Asp Trp Ser Pro Ser Leu Glu Leu Arg
        290                 295                 300

Thr Thr Glu Arg Ala Pro Thr His His His His His His His
305                 310                 315
```

<210> SEQ ID NO 2
<211> LENGTH: 118
<212> TYPE: PRT
<213> ORGANISM: artificial
<220> FEATURE:
<223> OTHER INFORMATION: VH of C1.2

<400> SEQUENCE: 2

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Tyr
            20                  25                  30

Trp Met Gly Trp Val Arg Gln Ala Pro Gly Lys Gly Leu Glu Trp Val
        35                  40                  45

Ser Ser Ile Ser Ser Ser Gly Gly Val Thr Pro Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Met Leu Gly Glu Leu Gly Trp Phe Asp Pro Trp Gly Gln Gly Thr
        100                 105                 110

Leu Val Thr Val Ser Ser
        115
```

<210> SEQ ID NO 3
<211> LENGTH: 107
<212> TYPE: PRT
<213> ORGANISM: artificial
<220> FEATURE:
<223> OTHER INFORMATION: VL of C1.2

<400> SEQUENCE: 3

```
Asp Ile Gln Met Thr Gln Ser Pro Ser Ala Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Ala Ser Asn Leu Gln Asn Gly Ile Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr His Cys Gln Gln Ser Tyr Ser Thr Pro Leu
            85                  90                  95

Thr Phe Gly Gly Gly Thr Asn Val Glu Ile Arg
        100                 105
```

<210> SEQ ID NO 4

```
<211> LENGTH: 118
<212> TYPE: PRT
<213> ORGANISM: artificial
<220> FEATURE:
<223> OTHER INFORMATION: VH of C1.2G

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Tyr
            20                  25                  30

Trp Met Gly Trp Val Arg Gln Ala Pro Gly Lys Gly Leu Glu Trp Val
        35                  40                  45

Ser Ser Ile Ser Ser Ser Gly Gly Val Thr Pro Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Gly Glu Leu Gly Trp Phe Asp Pro Trp Gly Gln Gly Thr
            100                 105                 110

Leu Val Thr Val Ser Ser
        115

<210> SEQ ID NO 5
<211> LENGTH: 107
<212> TYPE: PRT
<213> ORGANISM: artificial
<220> FEATURE:
<223> OTHER INFORMATION: VL  of C1.2G

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Ala Ser Asn Leu Gln Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 6
<211> LENGTH: 5
<212> TYPE: PRT
<213> ORGANISM: artificial
<220> FEATURE:
<223> OTHER INFORMATION: HCDR1 of C1.2

<400> SEQUENCE: 6

Leu Tyr Trp Met Gly
1               5

<210> SEQ ID NO 7
<211> LENGTH: 17
```

```
<212> TYPE: PRT
<213> ORGANISM: artificial
<220> FEATURE:
<223> OTHER INFORMATION: C1.2 HCDR2

<400> SEQUENCE: 7

Ser Ile Ser Ser Ser Gly Gly Val Thr Pro Tyr Ala Asp Ser Val Lys
1               5                   10                  15
Gly

<210> SEQ ID NO 8
<211> LENGTH: 9
<212> TYPE: PRT
<213> ORGANISM: artificial
<220> FEATURE:
<223> OTHER INFORMATION: C1.2 HCDR3

<400> SEQUENCE: 8

Leu Gly Glu Leu Gly Trp Phe Asp Pro
1               5

<210> SEQ ID NO 9
<211> LENGTH: 11
<212> TYPE: PRT
<213> ORGANISM: artificial
<220> FEATURE:
<223> OTHER INFORMATION: C1.2 LCDR1

<400> SEQUENCE: 9

Arg Ala Ser Gln Gly Ile Ser Ser Tyr Leu Asn
1               5                   10

<210> SEQ ID NO 10
<211> LENGTH: 6
<212> TYPE: PRT
<213> ORGANISM: artificial
<220> FEATURE:
<223> OTHER INFORMATION: C1.2 LCDR2

<400> SEQUENCE: 10

Ala Ser Asn Leu Gln Asn
1               5

<210> SEQ ID NO 11
<211> LENGTH: 9
<212> TYPE: PRT
<213> ORGANISM: artificial
<220> FEATURE:
<223> OTHER INFORMATION: C1.2 LCDR3

<400> SEQUENCE: 11

Gln Gln Ser Tyr Ser Thr Pro Leu Thr
1               5

<210> SEQ ID NO 12
<211> LENGTH: 8
<212> TYPE: PRT
<213> ORGANISM: artificial
<220> FEATURE:
<223> OTHER INFORMATION: consensus sequence of HCDR3 of C1.2
<220> FEATURE:
<221> NAME/KEY: VARIANT
<222> LOCATION: (5)..(5)
<223> OTHER INFORMATION: X is an amino acid selected from the group
      consisting of tryptophan, glutamine, methionine, serine,
      phenylalanine, glutamic acid and histidine
<220> FEATURE:
<221> NAME/KEY: VARIANT
```

```
<222> LOCATION: (6)..(6)
<223> OTHER INFORMATION: X is an amino acid selected from the group
      consisting of phenylalanine, tyrosine, methionine, serine, glycine
      and isoleucine
<220> FEATURE:
<221> NAME/KEY: VARIANT
<222> LOCATION: (7)..(7)
<223> OTHER INFORMATION: X is an amino acid selected from the group
      consisting of aspartic acid, methionine, glutamine, serine,
      leucine, valine, arginine and histidine
<220> FEATURE:
<221> NAME/KEY: VARIANT
<222> LOCATION: (8)..(8)
<223> OTHER INFORMATION: X is an amino acid selected from the group
      consisting of proline glutamic acid, alanine, leucine,
      phenylalanine, tyronis, threonine, asparagine, aspartic acid,
      serine, glycine, arginine, lysine

<400> SEQUENCE: 12

Leu Gly Glu Leu Xaa Xaa Xaa Xaa
1               5

<210> SEQ ID NO 13
<211> LENGTH: 9
<212> TYPE: PRT
<213> ORGANISM: artificial
<220> FEATURE:
<223> OTHER INFORMATION: consensus sequence of LCDR3 of C1.2
<220> FEATURE:
<221> NAME/KEY: VARIANT
<222> LOCATION: (1)..(1)
<223> OTHER INFORMATION: X is an amino acid selected from the group
      consisting of glutamine, glutamic acid, histidine, alanine or
      serine
<220> FEATURE:
<221> NAME/KEY: VARIANT
<222> LOCATION: (2)..(2)
<223> OTHER INFORMATION: X is an amino acid selected from the group
      consisting of glutamine, valine, phenylalanine, asparagine and
      glutamic acid
<220> FEATURE:
<221> NAME/KEY: VARIANT
<222> LOCATION: (3)..(3)
<223> OTHER INFORMATION: X is an amino acid selected from the group
      consisting of serine or glycine
<220> FEATURE:
<221> NAME/KEY: VARIANT
<222> LOCATION: (4)..(4)
<223> OTHER INFORMATION: X is an amino acid selected from the group
      consisting of tryptophan, methionine, phenylalanine, tyrosine,
      isoleucine and leucine
<220> FEATURE:
<221> NAME/KEY: VARIANT
<222> LOCATION: (5)..(5)
<223> OTHER INFORMATION: X is an amino acid selected from the group
      consisting of glutamic acid, methionine, glutamine, tryptophan,
      serine, valine, asparagine, glycine, alanine, arganine, histidine,
      tyrosine, lysine or threonine
<220> FEATURE:
<221> NAME/KEY: VARIANT
<222> LOCATION: (6)..(6)
<223> OTHER INFORMATION: X is an amino acid selected from the group
      consisting of tyrosine, methionine, isoleucine or threonine
<220> FEATURE:
<221> NAME/KEY: VARIANT
<222> LOCATION: (7)..(7)
<223> OTHER INFORMATION: X is an amino acid selected from the group
      consisting of proline, alanine, histidine, glycine and lysine
<220> FEATURE:
<221> NAME/KEY: VARIANT
<222> LOCATION: (8)..(8)
<223> OTHER INFORMATION: X is an amino acid selected from the group
      consisting of leucine, glutamine, methionine, alanine,
      phenylalanine, isoleucine, lysine, histidine and glycine
<220> FEATURE:
<221> NAME/KEY: VARIANT
<222> LOCATION: (9)..(9)
```

-continued

<223> OTHER INFORMATION: X is an amino acid selected from the group
      consisting of threonine, phenylalanine, tyrosine, methionine,
      lysine, serine, histidine, proline, tryptophan, isoleucine,
      glutamine, glycine and valine

<400> SEQUENCE: 13

Xaa Xaa Xaa Xaa Xaa Xaa Xaa Xaa Xaa
1               5

<210> SEQ ID NO 14
<211> LENGTH: 445
<212> TYPE: PRT
<213> ORGANISM: artificial
<220> FEATURE:
<223> OTHER INFORMATION: C1.2G heavy chain IgG4 with S241P mutation

<400> SEQUENCE: 14

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Tyr
            20                  25                  30

Trp Met Gly Trp Val Arg Gln Ala Pro Gly Lys Gly Leu Glu Trp Val
        35                  40                  45

Ser Ser Ile Ser Ser Ser Gly Val Thr Pro Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Gly Glu Leu Gly Trp Phe Asp Pro Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
            435                 440                 445

<210> SEQ ID NO 15
<211> LENGTH: 214
<212> TYPE: PRT
<213> ORGANISM: artificial
<220> FEATURE:
<223> OTHER INFORMATION: C1.2G with kappa light chain

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Ala Ser Asn Leu Gln Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 16

<211> LENGTH: 836
<212> TYPE: PRT
<213> ORGANISM: Homo sapiens

<400> SEQUENCE: 16

```
Met Ala Arg Leu Gly Asn Cys Ser Leu Thr Trp Ala Ala Leu Ile Ile
1               5                   10                  15

Leu Leu Leu Pro Gly Ser Leu Glu Glu Cys Gly His Ile Ser Val Ser
            20                  25                  30

Ala Pro Ile Val His Leu Gly Asp Pro Ile Thr Ala Ser Cys Ile Ile
        35                  40                  45

Lys Gln Asn Cys Ser His Leu Asp Pro Glu Pro Gln Ile Leu Trp Arg
    50                  55                  60

Leu Gly Ala Glu Leu Gln Pro Gly Gly Arg Gln Gln Arg Leu Ser Asp
65                  70                  75                  80

Gly Thr Gln Glu Ser Ile Ile Thr Leu Pro His Leu Asn His Thr Gln
                85                  90                  95

Ala Phe Leu Ser Cys Cys Leu Asn Trp Gly Asn Ser Leu Gln Ile Leu
            100                 105                 110

Asp Gln Val Glu Leu Arg Ala Gly Tyr Pro Pro Ala Ile Pro His Asn
        115                 120                 125

Leu Ser Cys Leu Met Asn Leu Thr Thr Ser Ser Leu Ile Cys Gln Trp
    130                 135                 140

Glu Pro Gly Pro Glu Thr His Leu Pro Thr Ser Phe Thr Leu Lys Ser
145                 150                 155                 160

Phe Lys Ser Arg Gly Asn Cys Gln Thr Gln Gly Asp Ser Ile Leu Asp
                165                 170                 175

Cys Val Pro Lys Asp Gly Gln Ser His Cys Cys Ile Pro Arg Lys His
            180                 185                 190

Leu Leu Leu Tyr Gln Asn Met Gly Ile Trp Val Gln Ala Glu Asn Ala
        195                 200                 205

Leu Gly Thr Ser Met Ser Pro Gln Leu Cys Leu Asp Pro Met Asp Val
    210                 215                 220

Val Lys Leu Glu Pro Pro Met Leu Arg Thr Met Asp Pro Ser Pro Glu
225                 230                 235                 240

Ala Ala Pro Pro Gln Ala Gly Cys Leu Gln Leu Cys Trp Glu Pro Trp
                245                 250                 255

Gln Pro Gly Leu His Ile Asn Gln Lys Cys Glu Leu Arg His Lys Pro
            260                 265                 270

Gln Arg Gly Glu Ala Ser Trp Ala Leu Val Gly Pro Leu Pro Leu Glu
        275                 280                 285

Ala Leu Gln Tyr Glu Leu Cys Gly Leu Leu Pro Ala Thr Ala Tyr Thr
    290                 295                 300

Leu Gln Ile Arg Cys Ile Arg Trp Pro Leu Pro Gly His Trp Ser Asp
305                 310                 315                 320

Trp Ser Pro Ser Leu Glu Leu Arg Thr Thr Glu Arg Ala Pro Thr Val
                325                 330                 335

Arg Leu Asp Thr Trp Trp Arg Gln Arg Gln Leu Asp Pro Arg Thr Val
            340                 345                 350

Gln Leu Phe Trp Lys Pro Val Pro Leu Glu Glu Asp Ser Gly Arg Ile
        355                 360                 365

Gln Gly Tyr Val Val Ser Trp Arg Pro Ser Gly Gln Ala Gly Ala Ile
    370                 375                 380

Leu Pro Leu Cys Asn Thr Thr Glu Leu Ser Cys Thr Phe His Leu Pro
```

-continued

```
            385                 390                 395                 400
        Ser Glu Ala Gln Glu Val Ala Leu Val Ala Tyr Asn Ser Ala Gly Thr
                        405                 410                 415

Ser Arg Pro Thr Pro Val Val Phe Ser Glu Ser Arg Gly Pro Ala Leu
                        420                 425                 430

Thr Arg Leu His Ala Met Ala Arg Asp Pro His Ser Leu Trp Val Gly
                        435                 440                 445

Trp Glu Pro Pro Asn Pro Trp Pro Gln Gly Tyr Val Ile Glu Trp Gly
                        450                 455                 460

Leu Gly Pro Pro Ser Ala Ser Asn Ser Asn Lys Thr Trp Arg Met Glu
        465                 470                 475                 480

Gln Asn Gly Arg Ala Thr Gly Phe Leu Leu Lys Glu Asn Ile Arg Pro
                        485                 490                 495

Phe Gln Leu Tyr Glu Ile Ile Val Thr Pro Leu Tyr Gln Asp Thr Met
                        500                 505                 510

Gly Pro Ser Gln His Val Tyr Ala Tyr Ser Gln Glu Met Ala Pro Ser
                        515                 520                 525

His Ala Pro Glu Leu His Leu Lys His Ile Gly Lys Thr Trp Ala Gln
                        530                 535                 540

Leu Glu Trp Val Pro Glu Pro Pro Glu Leu Gly Lys Ser Pro Leu Thr
        545                 550                 555                 560

His Tyr Thr Ile Phe Trp Thr Asn Ala Gln Asn Gln Ser Phe Ser Ala
                        565                 570                 575

Ile Leu Asn Ala Ser Ser Arg Gly Phe Val Leu His Gly Leu Glu Pro
                        580                 585                 590

Ala Ser Leu Tyr His Ile His Leu Met Ala Ala Ser Gln Ala Gly Ala
                        595                 600                 605

Thr Asn Ser Thr Val Leu Thr Leu Met Thr Leu Thr Pro Glu Gly Ser
                        610                 615                 620

Glu Leu His Ile Ile Leu Gly Leu Phe Gly Leu Leu Leu Leu Leu Thr
        625                 630                 635                 640

Cys Leu Cys Gly Thr Ala Trp Leu Cys Cys Ser Pro Asn Arg Lys Asn
                        645                 650                 655

Pro Leu Trp Pro Ser Val Pro Asp Pro Ala His Ser Ser Leu Gly Ser
                        660                 665                 670

Trp Val Pro Thr Ile Met Glu Glu Asp Ala Phe Gln Leu Pro Gly Leu
                        675                 680                 685

Gly Thr Pro Pro Ile Thr Lys Leu Thr Val Leu Glu Glu Asp Glu Lys
        690                 695                 700

Lys Pro Val Pro Trp Glu Ser His Asn Ser Ser Glu Thr Cys Gly Leu
        705                 710                 715                 720

Pro Thr Leu Val Gln Thr Tyr Val Leu Gln Gly Asp Pro Arg Ala Val
                        725                 730                 735

Ser Thr Gln Pro Gln Ser Gln Ser Gly Thr Ser Asp Gln Val Leu Tyr
                        740                 745                 750

Gly Gln Leu Leu Gly Ser Pro Thr Ser Pro Gly Pro Gly His Tyr Leu
                        755                 760                 765

Arg Cys Asp Ser Thr Gln Pro Leu Leu Ala Gly Leu Thr Pro Ser Pro
        770                 775                 780

Lys Ser Tyr Glu Asn Leu Trp Phe Gln Ala Ser Pro Leu Gly Thr Leu
        785                 790                 795                 800

Val Thr Pro Ala Pro Ser Gln Glu Asp Asp Cys Val Phe Gly Pro Leu
                        805                 810                 815
```

```
Leu Asn Phe Pro Leu Leu Gln Gly Ile Arg Val His Gly Met Glu Ala
            820                 825                 830

Leu Gly Ser Phe
        835

<210> SEQ ID NO 17
<211> LENGTH: 319
<212> TYPE: PRT
<213> ORGANISM: artificial
<220> FEATURE:
<223> OTHER INFORMATION: Ig and CRH domains of Macaca fascicularis
      G-CSFR (cynoG-CSFR) with a C-terminal polyhistidine tag

<400> SEQUENCE: 17

Glu Cys Gly His Ile Ser Val Ser Ala Pro Ile Val His Leu Gly Asp
1               5                   10                  15

Pro Ile Thr Ala Ser Cys Ile Ile Lys Gln Asn Cys Ser His Leu Asp
            20                  25                  30

Leu Glu Pro Gln Ile Leu Trp Arg Leu Gly Ala Glu Leu Gln Pro Gly
        35                  40                  45

Gly Arg Gln Gln Arg Leu Ser Asp Gly Ser Gln Gln Ser Thr Ile Thr
    50                  55                  60

Leu Pro His Leu Asn His Thr Arg Ala Phe Leu Ser Cys Ala Leu Asn
65                  70                  75                  80

Trp Gly Asn Ser Leu Gln Ile Leu Asp Gln Val Glu Leu Arg Ala Gly
                85                  90                  95

Tyr Pro Pro Ala Val Pro Arg Asn Leu Ser Cys Leu Met Asn Leu Thr
            100                 105                 110

Thr Ser Ser Leu Ile Cys Gln Trp Glu Pro Gly Pro Glu Thr His Leu
        115                 120                 125

Pro Thr Ser Phe Thr Leu Lys Ser Phe Lys Ser Arg Gly Asn Cys Gln
    130                 135                 140

Thr Gln Gly Asp Ser Ile Met Asp Cys Val Pro Glu Asp Gly Gln Ser
145                 150                 155                 160

His Cys Ser Ile Pro Arg Arg His Leu Leu Leu Tyr Gln Asn Met Gly
                165                 170                 175

Ile Trp Val Gln Ala Glu Asn Ala Leu Gly Thr Ser Met Ser Pro Gln
            180                 185                 190

Leu Cys Leu Glu Pro Met Asp Val Val Lys Leu Glu Pro Pro Met Leu
        195                 200                 205

Arg Thr Met Asp Pro Ser Pro Glu Ala Ala Pro Pro Gln Ala Gly Cys
    210                 215                 220

Leu Gln Leu Ser Trp Glu Pro Trp Gln Pro Ala Leu His Ile Asn Gln
225                 230                 235                 240

Lys Cys Glu Leu Arg His Lys Pro Gln Ser Gly Glu Ala Ser Trp Ala
                245                 250                 255

Leu Val Gly Pro Leu Pro Leu Glu Ala Leu Arg Tyr Glu Leu Cys Gly
            260                 265                 270

Leu Leu Pro Ala Thr Ala Tyr Thr Leu Gln Ile Arg Cys Ile Arg Trp
        275                 280                 285

Pro Leu Pro Gly His Trp Ser Asn Trp Ser Pro Ser Leu Glu Leu Arg
    290                 295                 300

Thr Thr Glu Arg Ala Pro Thr His His His His His His
305                 310                 315
```

```
<210> SEQ ID NO 18
<211> LENGTH: 444
<212> TYPE: PRT
<213> ORGANISM: artificial
<220> FEATURE:
<223> OTHER INFORMATION: C1.2G heavy chain IgG4 with S241P mutation and
      lacking C-terminal lysine residue

<400> SEQUENCE: 18
```

| | | | | | | | | | | | | | | |
|---|---|---|---|---|---|---|---|---|---|---|---|---|---|---|
| Glu | Val | Gln | Leu | Leu | Glu | Ser | Gly | Gly | Gly | Leu | Val | Gln | Pro | Gly |
| 1 | | | | 5 | | | | | 10 | | | | | 15 |
| Gly | | | | | | | | | | | | | | |
| Ser | Leu | Arg | Leu | Ser | Cys | Ala | Ala | Ser | Gly | Phe | Thr | Phe | Ser | Leu |
| | | 20 | | | | 25 | | | | | 30 | | | |
| Tyr | | | | | | | | | | | | | | |
| Trp | Met | Gly | Trp | Val | Arg | Gln | Ala | Pro | Gly | Lys | Gly | Leu | Glu | Trp |
| | | 35 | | | | 40 | | | | | 45 | | | |
| Val | | | | | | | | | | | | | | |
| Ser | Ser | Ile | Ser | Ser | Ser | Gly | Gly | Val | Thr | Pro | Tyr | Ala | Asp | Ser |
| 50 | | | | | 55 | | | | | 60 | | | | |
| Val | | | | | | | | | | | | | | |
| Lys | Gly | Arg | Phe | Thr | Ile | Ser | Arg | Asp | Asn | Ser | Lys | Asn | Thr | Leu |
| 65 | | | | | 70 | | | | | 75 | | | | 80 |
| Tyr | | | | | | | | | | | | | | |
| Leu | Gln | Met | Asn | Ser | Leu | Arg | Ala | Glu | Asp | Thr | Ala | Val | Tyr | Tyr |
| | | | | 85 | | | | | 90 | | | | | 95 |
| Cys | | | | | | | | | | | | | | |
| Ala | Lys | Leu | Gly | Glu | Leu | Gly | Trp | Phe | Asp | Pro | Trp | Gly | Gln | Gly |
| | | | 100 | | | | | 105 | | | | | 110 | |
| Thr | | | | | | | | | | | | | | |
| Leu | Val | Thr | Val | Ser | Ser | Ala | Ser | Thr | Lys | Gly | Pro | Ser | Val | Phe |
| | | 115 | | | | | 120 | | | | | 125 | | |
| Pro | | | | | | | | | | | | | | |
| Leu | Ala | Pro | Cys | Ser | Arg | Ser | Thr | Ser | Glu | Ser | Thr | Ala | Ala | Leu |
| 130 | | | | | 135 | | | | | 140 | | | | |
| Gly | | | | | | | | | | | | | | |
| Cys | Leu | Val | Lys | Asp | Tyr | Phe | Pro | Glu | Pro | Val | Thr | Val | Ser | Trp |
| 145 | | | | | 150 | | | | | 155 | | | | 160 |
| Asn | | | | | | | | | | | | | | |
| Ser | Gly | Ala | Leu | Thr | Ser | Gly | Val | His | Thr | Phe | Pro | Ala | Val | Leu |
| | | | | 165 | | | | | 170 | | | | | 175 |
| Gln | | | | | | | | | | | | | | |
| Ser | Ser | Gly | Leu | Tyr | Ser | Leu | Ser | Ser | Val | Val | Thr | Val | Pro | Ser |
| | | | 180 | | | | | 185 | | | | | 190 | |
| Ser | | | | | | | | | | | | | | |
| Ser | Leu | Gly | Thr | Lys | Thr | Tyr | Thr | Cys | Asn | Val | Asp | His | Lys | Pro |
| | | | 195 | | | | | 200 | | | | | 205 | |
| Ser | | | | | | | | | | | | | | |
| Asn | Thr | Lys | Val | Asp | Lys | Arg | Val | Glu | Ser | Lys | Tyr | Gly | Pro | Pro |
| | 210 | | | | | 215 | | | | | 220 | | | |
| Cys | | | | | | | | | | | | | | |
| Pro | Pro | Cys | Pro | Ala | Pro | Glu | Phe | Leu | Gly | Gly | Pro | Ser | Val | Phe |
| 225 | | | | | 230 | | | | | 235 | | | | 240 |
| Leu | | | | | | | | | | | | | | |
| Phe | Pro | Pro | Lys | Pro | Lys | Asp | Thr | Leu | Met | Ile | Ser | Arg | Thr | Pro |
| | | | 245 | | | | | 250 | | | | | 255 | |
| Glu | | | | | | | | | | | | | | |
| Val | Thr | Cys | Val | Val | Val | Asp | Val | Ser | Gln | Glu | Asp | Pro | Glu | Val |
| | | | 260 | | | | | 265 | | | | | 270 | |
| Gln | | | | | | | | | | | | | | |
| Phe | Asn | Trp | Tyr | Val | Asp | Gly | Val | Glu | Val | His | Asn | Ala | Lys | Thr |
| | | 275 | | | | | 280 | | | | | 285 | | |
| Lys | | | | | | | | | | | | | | |
| Pro | Arg | Glu | Glu | Gln | Phe | Asn | Ser | Thr | Tyr | Arg | Val | Val | Ser | Val |
| 290 | | | | | 295 | | | | | 300 | | | | |
| Leu | | | | | | | | | | | | | | |
| Thr | Val | Leu | His | Gln | Asp | Trp | Leu | Asn | Gly | Lys | Glu | Tyr | Lys | Cys |
| 305 | | | | | 310 | | | | | 315 | | | | 320 |
| Lys | | | | | | | | | | | | | | |
| Val | Ser | Asn | Lys | Gly | Leu | Pro | Ser | Ser | Ile | Glu | Lys | Thr | Ile | Ser |
| | | | | 325 | | | | | 330 | | | | | 335 |
| Lys | | | | | | | | | | | | | | |
| Ala | Lys | Gly | Gln | Pro | Arg | Glu | Pro | Gln | Val | Tyr | Thr | Leu | Pro | Pro |
| | | | 340 | | | | | 345 | | | | | 350 | |
| Ser | | | | | | | | | | | | | | |
| Gln | Glu | Glu | Met | Thr | Lys | Asn | Gln | Val | Ser | Leu | Thr | Cys | Leu | Val |
| | | | | 355 | | | | | 360 | | | | | 365 |
| Lys | | | | | | | | | | | | | | |

```
Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
                420             425                 430

His Tyr Thr Gln Lys Ser Leu Ser Leu Ser Leu Gly
            435                 440
```

METHOD OF TREATING ASTHMA

RELATED APPLICATION DATA

This application claims priority from Australian Patent Application No 2018900961 filed on 23 Mar. 2018 and entitled "Method of treating asthma". The entire contents of that application are hereby incorporated by reference.

INCORPORATION BY REFERENCE OF SEQUENCE LISTING

The Sequence Listing in an ASCII text file, named as 38828 Sequence Listing.txt of 31 KB, created on Sep. 18, 2020, and submitted to the United States Patent and Trademark Office via EFS-Web, is incorporated herein by reference.

FIELD

The present disclosure relates to methods of treating asthma in a subject.

BACKGROUND

Asthma is a common chronic respiratory condition characterized by variable and recurring symptoms, reversible airway obstruction, airway (e.g., bronchial) hyper-responsiveness, and an underlying inflammation. Acute symptoms of asthma include cough, wheezing, shortness of breath and nocturnal awakening. These symptoms usually arise from bronchospasm and require and respond to bronchodilator therapy. Central to the pathophysiology of asthma is the presence of underlying airway inflammation mediated by the recruitment and activation of multiple cell types including mast cells, eosinophils, neutrophils, T lymphocytes, macrophages, and dendritic cells. The mechanisms influencing airway hyper-responsiveness are multiple and include inflammation, dysfunctional neuroregulation, and airway remodeling. Airway remodeling involves structural changes including thickening of the sub-basement membrane, sub-epithelial fibrosis, airway smooth muscle hypertrophy and hyperplasia, blood vessel proliferation and dilation with consequent permanent changes in the airway that increase airflow obstruction.

Current treatments for asthma are aimed at controlling symptoms through medication. These medications include antiallergic compounds of various chemical and therapeutical classes, such as, for example, anti-inflammatory substances, leukotriene inhibitors, bronchodilators, cromolyn sodium and amino- or theophylline. Patients with mild asthma, i.e. having infrequent attacks, may use bronchodilators as needed while those with more frequent attacks, e.g. symptoms occurring more than twice per week, are typically treated with inhaled corticosteroids and/or bronchodilators. Severe asthma requires a medical evaluation and may require hospitalization, oxygen, and intravenous medications.

Granulocyte-colony stimulating factor (G-CSF) promotes expansion and maturation of neutrophil populations and has been investigated as a potential therapeutic agent for the treatment of allergic pulmonary inflammation, see Queto et al., Life Sciences (2011) 88:830-838. These studies have shown that administering G-CSF suppresses lung inflammation and down-modulates cytokine and eosinophil production, suggesting that G-CSF or an agonist thereof may be a suitable therapeutic for the treatment of asthma.

However, there generally remains a need to improve the presently available medication in order to better control the symptoms and to ameliorate the underlying disease processes in order to meet the therapeutic challenge of treating asthma.

SUMMARY

In producing the present invention, the inventors proceeded against prior teachings that G-CSF may have a protective role in allergic pulmonary inflammation and instead studied the effects of inhibiting G-CSF signaling in asthma. The inventors found that by administering a compound that inhibits G-CSF signaling, the effects of asthma were reduced. These findings provide the basis for methods for treating a subject with asthma by inhibiting G-CSF signaling.

Accordingly, in an example, the present disclosure provides a method for treating asthma in a subject, the method comprising administering a compound that inhibits G-CSF signaling.

The present disclosure also provides a compound that inhibits G-CSF signaling for use in the treatment of asthma.

The present disclosure also provides use of a compound that inhibits G-CSF signaling in the manufacture of a medicament for treatment of asthma.

In one example, the asthma is allergic asthma.
In one example, the asthma is neutrophilic asthma.
In one example, the asthma is mixed granulocytic asthma.
In one example, the asthma is severe asthma.
In one example, the asthma is moderate asthma. In one example, the asthma is moderate or severe asthma. In one example, the asthma is poorly controlled or uncontrolled asthma. In one example, the asthma is refractory asthma. In one example, the asthma is chronic asthma.

In one example, the subject is a human. In one example, the subject is an adult, for example over 18 years of age. In one example, the subject is a child, for example less than 18 years of age. In one example, the subject is between 5 and 35 years of age In one example, the subject is between 18 and 35 years of age.

In one example, the subject does not have chronic obstructive pulmonary disease (COPD).

In one example, the subject has airway bacterial colonisation. In one example, the subject has lower airway bacterial colonisation. In one example, the subject had airway bacterial colonisation during infancy, for example between 0 and 2 years of age. In one example, the subject had airway bacterial colonisation during childhood, for example between 0 and 18 years of age.

In one example, the subject has a respiratory viral infection. In one example, the viral infection is an influenza virus infection.

In one example, the subject has airway bacterial colonisation and a respiratory viral infection.

In one example, the methods described herein further comprise identifying the subject as being responsive to treatment with a compound that inhibits G-CSF signaling. In one example, identifying the subject as being responsive to treatment with a compound that inhibits G-CSF signaling comprises determining that the subject has increased levels of neutrophils in sputum. In one example, identifying the subject as being responsive to treatment with a compound that inhibits G-CSF signaling comprises determining that the subject has neutrophil levels in sputum of greater than 40% of sputum cells. In one example, identifying the subject as being responsive to treatment with a compound that inhibits G-CSF signaling comprises determining that the subject has neutrophil levels in sputum of greater than 60% of sputum cells. In one example, identifying the subject as being responsive to treatment with a compound that inhibits G-CSF signaling comprises determining that the subject has increased expression of G-CSF and/or G-CSFR in bronchial biopsy tissue.

In one example, a method of the disclosure comprises treating a subject previously shown to have increased levels of neutrophils in sputum and/or have increased expression of G-CSF and/or G-CSFR in bronchial biopsy tissue, e.g., as described herein.

In one example, the compound that inhibits G-CSF signaling is administered in an amount sufficient to reduce or prevent lung inflammation. In one example, the compound that inhibits G-CSF signaling is administered in an amount sufficient to reduce or prevent neutrophilic lung inflammation. In one example, the compound that inhibits G-CSF signaling is administered in an amount sufficient to reduce or prevent eosinophilic lung inflammation.

In one example, the compound that inhibits G-CSF signaling is administered in an amount sufficient to enhance lung function. In one example, the compound that inhibits G-CSF signaling is administered in an amount sufficient to increase FEV (forced expiratory volume in one second), e.g., compared to the FEVs in the subject before the compound was administered. In one example, the compound that inhibits G-CSF signaling is administered in an amount sufficient to increase FVC (forced vital capacity), e.g., compared to the FVC in the subject before the compound was administered.

In one example, the compound that inhibits G-CSF signaling is administered in an amount sufficient to reduce or prevent airway hyper-responsiveness (AHR).

In one example, the compound that inhibits G-CSF signaling is administered in an amount sufficient to reduce or prevent an increase in mucus production, e.g., compared to a subject to which the compound has not been administered.

In one example, the compound that inhibits G-CSF signaling is administered in an amount sufficient to have one or more of the following effects in the subject's lung:
(i) reduce or prevent an increase in neutrophil levels;
(ii) reduce or prevent an increase in neutrophil elastase levels;
(iii) reduce or prevent an increase in extracellular double stranded DNA levels;
(iv) reduce or prevent an increase in eosinophil levels; and
(v) reduce or prevent an increase in $T_H2$ cell levels.

In one example, the compound that inhibits G-CSF signaling is administered in an amount sufficient to reduce or prevent an increase in neutrophil levels, e.g., in the subject's lungs.

In one example, the compound that inhibits G-CSF signaling is administered in an amount sufficient to reduce or prevent an increase in neutrophil elastase levels, e.g., in the subject's lungs.

In one example, the compound that inhibits G-CSF signaling is administered in an amount sufficient to reduce or prevent an increase in extracellular double stranded DNA levels, e.g., in the subject's lungs.

In one example, the compound that inhibits G-CSF signaling is administered in an amount sufficient to reduce or prevent an increase in eosinophil levels, e.g., in the subject's lungs.

In one example, the compound that inhibits G-CSF signaling is administered in an amount sufficient to reduce or prevent an increase in $T_H2$ cell levels, e.g., in the subject's lungs.

In one example, the compound that inhibits G-CSF signaling is administered in an amount sufficient to prevent or reduce the severity of an asthma exacerbation. Thus, in one example, administering the compound that inhibits G-CSF signaling prevents or reduces the severity of an asthma exacerbation.

Methods for assessing each of the foregoing are known in the art and/or described herein. Furthermore, a person skilled in the art will appreciate that the term "reduce" is used herein to refer to a lower amount of any of the items listed above, relative to either the amount in the subject prior to administration of the compound that inhibits G-CSF signaling, or relative to the amount in a corresponding control subject.

In one example, the compound that inhibits G-CSF signaling is administered in combination with another compound. In one example, the other compound is an anti-inflammatory compound. In one example, the other compound is an immunomodulator or an immunosuppressant. In one example, the other compound is a corticosteroid, e.g. a glucocorticoid. In one example, the other compound is a beta2 agonist. In one example, the other compound is a leukotriene receptor antagonist. In one example, the other compound is a muscarinic antagonist. In one example, the other compound is a theophylline. In one example, the other compound is magnesium sulfate. In one example, the other compound is a mast cell stabilizer. In one example, the other compound is an anti-IL-5 antibody, e.g., mepolizumab. In one example, the other compound is an anti-IgE antibody, e.g., omalizumab. In one example, the other compound is an anti-IL-17A antibody, e.g., secukinumab.

In some examples, the compound that inhibits G-CSF signaling is administered in combination with a cell. In some examples, the cell is a stem cell, such as a mesenchymal stem cell.

In some examples, the compound that inhibits G-CSF signaling is administered in combination with a gene therapy.

In one example, the compound that inhibits G-CSF signaling is administered simultaneously with the other compound. In one example, the compound that inhibits G-CSF signaling is administered before the other compound. In one example, the compound that inhibits G-CSF signaling is administered after the other compound.

In one example, the compound that inhibits G-CSF signaling binds to G-CSF or to G-CSF receptor (G-CSFR). In one example, the compound that inhibits G-CSF signaling binds to G-CSF. In one example, the compound that inhibits G-CSF signaling binds to G-CSF receptor (G-CSFR).

In one example, the compound that inhibits G-CSF signaling is a protein.

In one example, the compound that inhibits G-CSF signaling is a protein comprising an antibody variable region that binds to or specifically binds to G-CSFR and neutralizes G-CSF signaling. Reference herein to a protein or antibody that "binds to" G-CSFR provides literal support for a protein or antibody that "binds specifically to" G-CSFR.

In one example, the compound that inhibits G-CSF signaling is a protein comprising an antibody variable region that binds to or specifically binds to G-CSF and neutralizes G-CSF signaling. Reference herein to a protein or antibody that "binds to" G-CSF provides literal support for a protein or antibody that "binds specifically to" G-CSF.

In some examples, the compound that inhibits G-CSF signaling is a protein comprising a Fv. In some examples, the protein is selected from the group consisting of:
(i) a single chain Fv fragment (scFv);
(ii) a dimeric scFv (di-scFv); or
(iv) a diabody;
(v) a triabody;
(vi) a tetrabody;
(vii) a Fab;
(viii) a F(ab')$_2$;
(ix) a Fv;
(x) one of (i) to (ix) linked to a constant region of an antibody, Fc or a heavy chain constant domain ($C_H$) 2 and/or $C_H$3;
(xi) one of (i) to (ix) linked to albumin, functional fragments or variants thereof or a protein (e.g., antibody or antigen binding fragment thereof) that binds to albumin; or
(xii) an antibody.

In one example, the protein is an antibody. In one example, the antibody is a naked antibody. Exemplary antibodies are described in WO2012171057, which is incorporated herein by reference.

In one example, the protein is an antibody which binds to hG-CSFR expressed on the surface of a cell at an affinity of at least about 5 nM. In one example, the protein is an antibody which binds to hG-CSFR expressed on the surface of a cell at an affinity of at least about 4 nM. In one example, the protein is an antibody which binds to hG-CSFR expressed on the surface of a cell at an affinity of at least about 3 nM. In one example, the protein is an antibody which binds to hG-CSFR expressed on the surface of a cell at an affinity of at least about 2 nM. In one example, the protein is an antibody which binds to hG-CSFR expressed on the surface of a cell at an affinity of at least about 1 nM.

In one example, the protein is an antibody which inhibits G-CSF-induced proliferation of a BaF3 cell expressing hG-CSFR with an IC50 of at least about 5 nM. In one example, the protein is an antibody which inhibits G-CSF-induced proliferation of a BaF3 cell expressing hG-CSFR with an IC50 of at least about 4 nM. In one example, the protein is an antibody which inhibits G-CSF-induced proliferation of a BaF3 cell expressing hG-CSFR with an IC50 of at least about 3 nM. In one example, the protein is an antibody which inhibits G-CSF-induced proliferation of a BaF3 cell expressing hG-CSFR with an IC50 of at least about 2 nM. In one example, the protein is an antibody which inhibits G-CSF-induced proliferation of a BaF3 cell expressing hG-CSFR with an IC50 of at least about 1 nM. In one example, the protein is an antibody which inhibits G-CSF-induced proliferation of a BaF3 cell expressing hG-CSFR with an IC50 of at least about 0.5 nM.

In one example, the protein is chimeric, de-immunized, humanized, human or primatized. In one example, the protein or antibody is human.

In one example, the protein comprises an antibody variable region that competitively inhibits the binding of antibody C1.2G comprising a heavy chain variable region ($V_H$) comprising a sequence set forth in SEQ ID NO: 4 and a light chain variable region ($V_L$) comprising a sequence set forth in SEQ ID NO: 5 to G-CSFR.

In one example, the protein binds to an epitope comprising residues within one or two or three or four regions selected from 111-115, 170-176, 218-234 and/or 286-300 of SEQ ID NO: 1.

In one example, the protein is an antibody comprising a heavy chain variable region (VH) comprising an amino acid sequence set forth in SEQ ID NO: 4 and a light chain variable region (VL) comprising an amino acid sequence set forth in SEQ ID NO: 5.

In one example, the protein is an antibody comprising a VH comprising an amino acid sequence set forth in SEQ ID NO: 2 and a VL comprising an amino acid sequence set forth in SEQ ID NO: 3.

In one example, the protein is an antibody comprising a VH comprising three CDRs of a VH comprising an amino acid sequence set forth in SEQ ID NO: 4 and a VL comprising three CDRs of a VL comprising an amino acid sequence set forth in SEQ ID NO: 5.

In one example, the protein is an antibody comprising a VH comprising three CDRs of a VH comprising an amino acid sequence set forth in SEQ ID NO: 2 and a VL comprising three CDRs of a VL comprising an amino acid sequence set forth in SEQ ID NO: 3.

In one example, the protein is an antibody comprising:
(i) a heavy chain comprising an amino acid sequence set forth in SEQ ID NO: 14 or 18 and a light chain comprising an amino acid sequence set forth in SEQ ID NO: 15; or
(ii) one heavy chain comprising an amino acid sequence set forth in SEQ ID NO: 14 and one heavy chain comprising an amino acid sequence set forth in SEQ ID NO: 18 and two light chains comprising an amino acid sequence set forth in SEQ ID NO: 15.

KEY TO SEQUENCE LISTING

SEQ ID NO: 1—amino acids 25-335 of *Homo sapiens* G-CSFR (hG-CSFR) with a C-terminal polyhistidine tag
SEQ ID NO: 2—$V_H$ of C1.2
SEQ ID NO: 3—$V_L$ of C1.2
SEQ ID NO: 4—$V_H$ of C1.2G
SEQ ID NO: 5—$V_L$ of C1.2G
SEQ ID NO: 6—HCDR1 of C1.2
SEQ ID NO: 7—HCDR2 of C1.2
SEQ ID NO: 8—HCDR3 of C1.2
SEQ ID NO: 9—LCDR1 of C1.2
SEQ ID NO: 10—LCDR2 of C1.2
SEQ ID NO: 11—LCDR3 of C1.2
SEQ ID NO: 12—consensus sequence of HCDR3 of C1.2
SEQ ID NO: 13—consensus sequence of LCDR3 of C1.2
SEQ ID NO: 14—Heavy chain of C1.2G with stabilized IgG4 constant region
SEQ ID NO: 15—Light chain of C1.2G with kappa constant region
SEQ ID NO: 16—sequence of exemplary h-G-CSFR
SEQ ID NO: 17—polypeptide comprising Ig and CRH domains of *Macaca fascicularis* G-CSFR (cynoG-CSFR) with a C-terminal polyhistidine tag
SEQ ID NO: 18—Heavy chain of C1.2G with stabilized IgG4 constant region and lacking C-terminal lysine.

DETAILED DESCRIPTION

General

Figure 1:
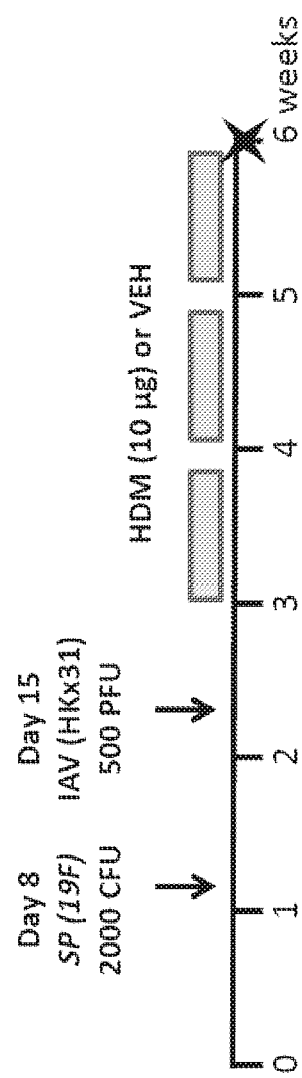
FIG. 1 is a timeline for production of an asthma model. Female BALB/c neonatal mice in litters consisting of 5—7 pups were inoculated intranasally with *S. pneumoniae* (SP; 2000 CFU) and/or influenza A virus (IAV; 500 PFU), where saline (SAL) was used as control. At 20-21 days of age, weaned female mice were sensitized to 10 μg house dust mite extract (HDM) aeroallergen or vehicle (VEH) 5 days per week over 3 weeks.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter.

Those skilled in the art will appreciate that the present disclosure is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only. Functionally-equivalent products, compositions and methods are clearly within the scope of the present disclosure.

Any example of the present disclosure herein shall be taken to apply mutatis mutandis to any other example of the disclosure unless specifically stated otherwise.

Unless specifically defined otherwise, all technical and scientific terms used herein shall be taken to have the same meaning as commonly understood by one of ordinary skill in the art (for example, in immunology, immunohistochemistry, protein chemistry, and biochemistry).

Unless otherwise indicated, the recombinant protein, cell culture, and immunological techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al. Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The description and definitions of variable regions and parts thereof, immunoglobulins, antibodies and fragments thereof herein may be further clarified by the discussion in Kabat *Sequences of Proteins of Immunological Interest*, National Institutes of Health, Bethesda, Md., 1987 and 1991, Bork et al., *J Mol. Biol.* 242, 309-320, 1994, Chothia and Lesk *J. Mol Biol.* 196:901-917, 1987, Chothia et al. *Nature* 342, 877-883, 1989 and/or or Al-Lazikani et al., *J Mol Biol* 273, 927-948, 1997.

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Selected Definitions

A "compound", as contemplated by the present disclosure, can take any of a variety of forms including natural compounds, chemical small molecule compounds or biological compounds or macromolecules. Exemplary compounds include an antibody or an antigen binding fragment of an antibody, a nucleic acid, a polypeptide, a peptide, and a small molecule.

Reference herein to "granulocyte colony-stimulating factor" (G-CSF) includes native forms of G-CSF, mutant forms thereof, e.g., filgrastim and pegylated forms of G-CSF or filgrastim. This term also encompasses mutant forms of G-CSF retaining activity to bind to G-CSFR (e.g., human G-CSFR) and induce signaling.

G-CSF is a major regulator of granulocyte production. G-CSF is produced by bone marrow stromal cells, endothelial cells, macrophages, and fibroblasts, and production is induced by inflammatory stimuli. G-CSF acts through the G-CSF receptor (G-CSFR), which is expressed on early myeloid progenitors, mature neutrophils, monocytes/macrophages, T and B lymphocytes and endothelial cells.

For the purposes of nomenclature only and not limitation, an exemplary sequence of a human G-CSFR is set out in NCBI Reference Sequence: NP_000751.1 (and set out in SEQ ID NO: 16). The sequence of G-CSFR from other species can be determined using sequences provided herein and/or in publically available databases and/or determined using standard techniques (e.g., as described in Ausubel et al., (editors), Current Protocols in Molecular Biology, Greene Pub. Associates and Wiley-Interscience (1988, including all updates until present) or Sambrook et al., Molecular Cloning: A Laboratory Manual, Cold Spring Harbor Laboratory Press (1989)) Reference to human G-CSFR may be abbreviated to hG-CSFR and reference to cynomolgus monkey G-CSFR may be abbreviated to cynoG-CSFR. Reference to soluble G-CSFR refers to polypeptides comprising the ligand binding region of G-CSFR. The Ig and CRH domains of the G-CSFR are involved in ligand binding and receptor dimerization (Layton et al., *J. Biol Chem.*, 272: 29735-29741, 1997 and Fukunaga et al, *EMBO J.* 10: 2855-2865, 1991). Soluble forms of G-CSFR comprising these portions of the receptor have been used in various studies of the receptor and mutation of the free cysteines at positions 78, 163, and 228 of the receptor assists in expression and isolation of the soluble receptor polypeptide (Mine et al., *Biochem.*, 43: 2458-2464 2004) without affecting ligand binding.

As used herein the term "asthma" will be understood to mean a disease characterized by paroxysmal or persistent symptoms of dyspnea, chest tightness, wheezing, sputum production and cough, associated with variable airflow limitation and airway hyper-responsiveness to endogenous or exogenous stimuli (Canadian Asthma Consensus Guidelines) and/or a condition characterized by airway hyper-responsiveness that leads to recurrent episodes of wheezing, breathlessness, chest tightness, and coughing, particularly at night or in the early morning along with variable airflow obstruction which is often reversible either spontaneously or with treatment (The Global Initiative for Asthma).

As used herein, the term "disease" or "condition" refers to a disruption of or interference with normal function, and is not to be limited to any specific condition, disease or disorder.

As used herein, the terms "treating", "treat" or "treatment" include administering a compound described herein to reduce, prevent, or eliminate at least one symptom of a specified disease or condition.

As used herein, the term "subject" shall be taken to mean any animal including humans, for example a mammal. Exemplary subjects include but are not limited to humans and non-human primates. In one example, the subject is a human.

The term "protein" shall be taken to include a single polypeptide chain, i.e., a series of contiguous amino acids linked by peptide bonds or a series of polypeptide chains covalently or non-covalently linked to one another (i.e., a polypeptide complex). For example, the series of polypeptide chains can be covalently linked using a suitable chemical or a disulphide bond. Examples of non-covalent bonds include hydrogen bonds, ionic bonds, Van der Waals forces, and hydrophobic interactions.

The term "polypeptide" or "polypeptide chain" will be understood from the foregoing paragraph to mean a series of contiguous amino acids linked by peptide bonds.

The term "isolated protein" or "isolated polypeptide" is a protein or polypeptide that by virtue of its origin or source of derivation is not associated with naturally-associated components that accompany it in its native state; is substantially free of other proteins from the same source. A protein may be rendered substantially free of naturally associated components or substantially purified by isolation, using protein purification techniques known in the art. By "substantially purified" is meant the protein is substantially free of contaminating agents, e.g., at least about 70% or 75% or 80% or 85% or 90% or 95% or 96% or 97% or 98% or 99% free of contaminating agents.

The term "recombinant" shall be understood to mean the product of artificial genetic recombination. Accordingly, in the context of a recombinant protein comprising an antibody antigen binding domain, this term does not encompass an antibody naturally-occurring within a subject's body that is the product of natural recombination that occurs during B cell maturation. However, if such an antibody is isolated, it is to be considered an isolated protein comprising an antibody antigen binding domain. Similarly, if nucleic acid encoding the protein is isolated and expressed using recombinant means, the resulting protein is a recombinant protein comprising an antibody antigen binding domain. A recombinant protein also encompasses a protein expressed by artificial recombinant means when it is within a cell, tissue or subject, e.g., in which it is expressed.

As used herein, the term "antigen binding site" shall be taken to mean a structure formed by a protein that is capable of binding or specifically binding to an antigen. The antigen binding site need not be a series of contiguous amino acids, or even amino acids in a single polypeptide chain. For example, in a Fv produced from two different polypeptide chains the antigen binding site is made up of a series of amino acids of a $V_L$ and a $V_H$ that interact with the antigen and that are generally, however not always in the one or more of the CDRs in each variable region. In some examples, an antigen binding site is a $V_H$ or a $V_L$ or a Fv.

The skilled artisan will be aware that an "antibody" is generally considered to be a protein that comprises a variable region made up of a plurality of polypeptide chains, e.g., a polypeptide comprising a $V_L$ and a polypeptide comprising a $V_H$. An antibody also generally comprises constant domains, some of which can be arranged into a constant region, which includes a constant fragment or fragment crystallizable (Fc), in the case of a heavy chain. A $V_H$ and a $V_L$ interact to form a Fv comprising an antigen binding region that is capable of specifically binding to one or a few closely related antigens. Generally, a light chain from mammals is either a κ light chain or a λ light chain and a heavy chain from mammals is α, δ, ε, γ, or μ. Antibodies can be of any type (e.g., IgG, IgE, IgM, IgD, IgA, and IgY), class (e.g., $IgG_1$, $IgG_2$, $IgG_3$, $IgG_4$, $IgA_1$ and $IgA_2$) or subclass. The term "antibody" also encompasses humanized antibodies, primatized antibodies, human antibodies and chimeric antibodies.

The terms "full-length antibody," "intact antibody" or "whole antibody" are used interchangeably to refer to an antibody in its substantially intact form, as opposed to an antigen binding fragment of an antibody. Specifically, whole antibodies include those with heavy and light chains including an Fc region. The constant domains may be wild-type sequence constant domains (e.g., human wild-type sequence constant domains) or amino acid sequence variants thereof.

As used herein, "variable region" refers to the portions of the light and/or heavy chains of an antibody as defined herein that is capable of specifically binding to an antigen and includes amino acid sequences of complementarity determining regions (CDRs); i.e., CDR1, CDR2, and CDR3, and framework regions (FRs). Exemplary variable regions comprise three or four FRs (e.g., FR1, FR2, FR3 and optionally FR4) together with three CDRs. In the case of a protein derived from an IgNAR, the protein may lack a CDR2. $V_H$ refers to the variable region of the heavy chain. $V_L$ refers to the variable region of the light chain.

As used herein, the term "complementarity determining regions" (syn. CDRs; i.e., CDR1, CDR2, and CDR3) refers to the amino acid residues of an antibody variable region the presence of which are necessary for antigen binding. Each variable region typically has three CDR regions identified as CDR1, CDR2 and CDR3. The amino acid positions assigned to CDRs and FRs can be defined according to Kabat *Sequences of Proteins of Immunological Interest*, National Institutes of Health, Bethesda, Md., 1987 and 1991 or other numbering systems in the performance of this disclosure, e.g., the canonical numbering system of Chothia and Lesk *J. Mol Biol.* 196: 901-917, 1987; Chothia et al. *Nature* 342, 877-883, 1989; and/or Al-Lazikani et al., *J Mol Biol* 273: 927-948, 1997; the IMGT numbering system of Lefranc et al., *Devel. And Compar. Immunol.*, 27: 55-77, 2003; or the AHO numbering system of Honnegher and Plükthun *J. Mol. Biol.*, 309: 657-670, 2001. For example, according to the numbering system of Kabat, $V_H$ framework regions (FRs) and CDRs are positioned as follows: residues 1-30 (FR1), 31-35 (CDR1), 36-49 (FR2), 50-65 (CDR2), 66-94 (FR3), 95-102 (CDR3) and 103-113 (FR4). According to the numbering system of Kabat, $V_L$ FRs and CDRs are positioned as follows: residues 1-23 (FR1), 24-34 (CDR1), 35-49 (FR2), 50-56 (CDR2), 57-88 (FR3), 89-97 (CDR3) and 98-107 (FR4). The present disclosure is not limited to FRs and CDRs as defined by the Kabat numbering system, but includes all numbering systems, including those discussed above. In one example, reference herein to a CDR (or a FR) is in respect of those regions according to the Kabat numbering system.

"Framework regions" (FRs) are those variable region residues other than the CDR residues.

As used herein, the term "Fv" shall be taken to mean any protein, whether comprised of multiple polypeptides or a single polypeptide, in which a $V_L$ and a $V_H$ associate and form a complex having an antigen binding site, i.e., capable of specifically binding to an antigen. The $V_H$ and the $V_L$ which form the antigen binding site can be in a single polypeptide chain or in different polypeptide chains. Furthermore, an Fv of the disclosure (as well as any protein of the disclosure) may have multiple antigen binding sites which may or may not bind the same antigen. This term shall be understood to encompass fragments directly derived from an antibody as well as proteins corresponding to such a fragment produced using recombinant means. In some examples, the $V_H$ is not linked to a heavy chain constant domain ($C_H$) 1 and/or the $V_L$ is not linked to a light chain constant domain ($C_L$). Exemplary Fv containing polypeptides or proteins include a Fab fragment, a Fab' fragment, a F(ab') fragment, a scFv, a diabody, a triabody, a tetrabody or higher order complex, or any of the foregoing linked to a constant region or domain thereof, e.g., $C_H2$ or $C_H3$ domain, e.g., a minibody. A "Fab fragment" consists of a monovalent antigen-binding fragment of an immunoglobulin, and can be produced by digestion of a whole antibody with the enzyme papain, to yield a fragment consisting of an intact light chain and a portion of a heavy chain or can be produced using recombinant means. A "Fab' fragment" of an antibody can be obtained by treating a whole antibody with pepsin, followed by reduction, to yield a molecule consisting of an intact light chain and a portion of a heavy chain comprising a $V_H$ and a single constant domain. Two Fab' fragments are obtained per antibody treated in this manner. A Fab' fragment can also be produced by recombinant means. A "F(ab')2 fragment" of an antibody consists of a dimer of two Fab' fragments held together by two disulfide bonds, and is obtained by treating a whole antibody molecule with the enzyme pepsin, without subsequent reduction. A "$Fab_2$" fragment is a recombinant fragment comprising two Fab fragments linked using, for example a leucine zipper or a $C_H3$ domain. A "single chain Fv" or "scFv" is a recombinant molecule containing the variable region fragment (Fv) of an antibody in which the variable region of the light chain and the variable region of the heavy chain are covalently linked by a suitable, flexible polypeptide linker.

As used herein, the term "binds" in reference to the interaction of a compound or an antigen binding site thereof with an antigen means that the interaction is dependent upon the presence of a particular structure (e.g., an antigenic determinant or epitope) on the antigen. For example, an antibody recognizes and binds to a specific protein structure rather than to proteins generally. If an antibody binds to epitope "A", the presence of a molecule containing epitope "A" (or free, unlabeled "A"), in a reaction containing labeled "A" and the protein, will reduce the amount of labeled "A" bound to the antibody.

As used herein, the term "specifically binds" or "binds specifically" shall be taken to mean that a compound of the disclosure reacts or associates more frequently, more rapidly, with greater duration and/or with greater affinity with a particular antigen or cell expressing same than it does with alternative antigens or cells. For example, a compound binds to G-CSFR (e.g., hG-CSFR) with materially greater affinity (e.g., 20 fold or 40 fold or 60 fold or 80 fold to 100 fold or 150 fold or 200 fold) than it does to other cytokine receptor or to antigens commonly recognized by polyreactive natural antibodies (i.e., by naturally occurring antibodies known to bind a variety of antigens naturally found in humans). Generally, but not necessarily, reference to binding means specific binding, and each term shall be understood to provide explicit support for the other term.

A protein or antibody may be considered to "preferentially bind" to a polypeptide if it binds that polypeptide with a dissociation constant ($K_D$) that is less than the protein's or antibody's $K_D$ for another polypeptide. In one example, a protein or antibody is considered to preferentially bind to a polypeptide if it binds the polypeptide with an affinity (i.e., $K_D$) that is at least about 20 fold or 40 fold or 60 fold or 80 fold or 100 fold or 120 fold or 140 fold or 160 fold more than the protein's or antibody's $K_D$ for another polypeptide.

For the purposes of clarification and as will be apparent to the skilled artisan based on the exemplified subject matter herein, reference to "affinity" in this specification is a reference to $K_D$ of a protein or antibody.

For the purposes of clarification and as will be apparent to the skilled artisan based on the description herein, reference to an "affinity of at least about" will be understood to mean that the affinity (or $K_D$) is equal to the recited value or higher (i.e., the value recited as the affinity is lower), i.e., an affinity of 2 nM is greater than an affinity of 3 nM. Stated another way, this term could be "an affinity of X or less", wherein X is a value recited herein.

An "$IC_{50}$ of at least about" will be understood to mean that the $IC_{50}$ is equal to the recited value or greater (i.e., the value recited as the $IC_{50}$ is lower), i.e., an $IC_{50}$ of 2 nM is greater than an $IC_{50}$ of 3 nM. Stated another way, this term could be "an $IC_{50}$ of X or less", wherein X is a value recited herein.

As used herein, the term "epitope" (syn. "antigenic determinant") shall be understood to mean a region of hG-CSFR to which a protein comprising an antigen binding site of an antibody binds. This term is not necessarily limited to the specific residues or structure to which the protein makes contact. For example, this term includes the region spanning amino acids contacted by the protein and/or 5-10 or 2-5 or 1-3 amino acids outside of this region. In some examples, the epitope comprises a series of discontinuous amino acids that are positioned close to one another when hG-CSFR is folded, i.e., a "conformational epitope". For example, a conformational epitope comprises amino acids in one or more or two or more or all of the regions corresponding to 111-115, 170-176, 218-234 and/or 286-300 of SEQ ID NO: 1. The skilled artisan will also be aware that the term "epitope" is not limited to peptides or polypeptides. For example, the term "epitope" includes chemically active surface groupings of molecules such as sugar side chains, phosphoryl side chains, or sulfonyl side chains, and, in certain examples, may have specific three dimensional structural characteristics, and/or specific charge characteristics.

The term "competitively inhibits" shall be understood to mean that a protein of the disclosure (or an antigen binding site thereof) reduces or prevents binding of a recited antibody or protein to G-CSFR, e.g., to hG-CSFR. This may be due to the protein (or antigen binding site) and antibody binding to the same or an overlapping epitope. It will be apparent from the foregoing that the protein need not completely inhibit binding of the antibody, rather it need only reduce binding by a statistically significant amount, for example, by at least about 10% or 20% or 30% or 40% or 50% or 60% or 70% or 80% or 90% or 95%. Preferably, the protein reduces binding of the antibody by at least about 30%, more preferably by at least about 50%, more preferably, by at least about 70%, still more preferably by at least about 75%, even more preferably, by at least about 80% or 85% and even more preferably, by at least about 90%. Methods for determining competitive inhibition of binding are known in the art and/or described herein. For example, the antibody is exposed to G-CSFR either in the presence or absence of the protein. If less antibody binds in the presence of the protein than in the absence of the protein, the protein is considered to competitively inhibit binding of the antibody. In one example, the competitive inhibition is not due to steric hindrance.

"Overlapping" in the context of two epitopes shall be taken to mean that two epitopes share a sufficient number of amino acid residues to permit a protein (or antigen binding site thereof) that binds to one epitope to competitively inhibit the binding of a protein (or antigen binding site) that binds to the other epitope. For example, the "overlapping" epitopes share at least 1 or 2 or 3 or 4 or 5 or 6 or 7 or 8 or 9 or 20 amino acids.

As used herein, the term "neutralize" shall be taken to mean that a compound is capable of blocking, reducing or preventing G-CSF-mediated signaling in a cell through the G-CSFR. Methods for determining neutralization are known in the art and/or described herein.

Treatment of Asthma

The present disclosure provides, for example, a method for treating asthma in a subject comprising administering a compound that inhibits granulocyte colony stimulating factor (G-CSF) signaling.

In the context of asthma, the term "treating" or "treat" refers to administering a compound described herein to reduce, eliminate, or prevent an occurrence or exacerbation of at least one symptom. For example, a compound described herein can be administered in order to prevent an asthmatic attack. Alternatively, or additionally, the compound can be administered to alleviate asthmatic symptoms such as wheezing, shortness of breath, chest tightness, and/or coughing.

In one example, the compound that inhibits G-CSF signaling is administered in an amount sufficient to prevent or reduce the severity of an asthma exacerbation. Thus, in one example, administering the compound that inhibits G-CSF signaling prevents or reduces the severity of an asthma exacerbation. As used herein, the term "asthma exacerbation" (also referred to as an "asthma attack") refers to an exaggerated lower airway response to an environmental stimulus which results in acute or subacute episode of progressively worsening shortness of breath, coughing, wheezing, or chest tightness or any combination thereof.

In one example, the asthma is allergic asthma. As used herein, the term "allergic asthma" (also referred to as "acute asthma") refers to asthma triggered by allergens (e.g., dust mite or pollen) activating mast cells located beneath the mucosa of the lower airways of respiratory tract. Activation of mast cells triggers release of granules that stimulate the nasal epithelium to produce mucus and subsequent contraction of smooth muscle within the airway. This contraction of smooth muscle constricts the airway, causing the asthmatic symptoms.

In one example, the asthma is neutrophilic asthma. As used herein, the term "neutrophilic asthma" refers to a subset of asthma that is characterized by an increase in the amount of neutrophils in the airways of a subject. Neutrophilic asthma can be categorized by high neutrophil counts in sputum, for example greater than 40% or greater than 60% of sputum cells. The response to treatment of neutrophilic asthma with corticosteroids is often found to be ineffective, compared to patients with eosinophilic asthma. Neutrophilic asthma is also associated with upregulated expression of IL-8, IL-17, and IFN-γ in the airways. In contrast, "eosinophilic asthma", which is characterised by an increase in the levels of eosinophils in the airways, is associated with an increase in IL-5 expression and a Th2-dominant inflammatory response.

In one example, the asthma is mixed granulocytic asthma. As used herein, the term "mixed granulocytic asthma" refers to asthma which is characterized by an increase in the amount of both neutrophils and eosinophils in the airways of a subject.

In one example, the asthma is severe asthma. As used herein, the term "severe asthma", refers to asthma for which symptoms are only partially controlled or even uncontrolled, despite intensive treatment with standard therapies. Severe asthma can be defined according the International ERS/ATS guidelines on definition, evaluation and treatment of severe asthma (Chung et al., Eur Respir J. 2014; 43(2):343-73). According to the ERS/ATS guidelines, severe asthma is defined as asthma which would require treatment with high dose inhaled corticosteroids (ICS) plus a second controller (eg a Long-acting 132 agonist, montelukast, or theophylline) and/or treatment with systemic corticosteroids to prevent it from becoming uncontrolled or which remains uncontrolled despite the treatment. Examples of high doses of inhaled corticosteroids according to the ERS/ATS guidelines are provided in Table 1.

TABLE 1 high dose of inhaled corticosteroids
(ICS) according to ERS/ATS guidelines

|  | 6 to 12 years | >12 years |
| --- | --- | --- |
| Beclomethasone | ≥800 μg*¹ | ≥2000 μg*¹ |
|  | ≥320 μg*² | ≥1000 μg*² |
| Budesonide | ≥800 μg | ≥1600 μg |
| Ciclesonide | ≥160 μg | ≥320 μg |
| Fluticasone propionate | ≥500 μg | ≥1000 μg |
| Mometasone furoate | ≥500 μg | ≥800 μg |

*¹Beclomethasone dose for dry powder inhalers
*²Beclomethasone for hydrofluoroalkane (HFA) metered-dose inhalers In one example, the asthma is moderate asthma. In one example, the asthma is moderate or severe asthma. Asthma is classified as "moderate" if symptoms occur daily, symptoms exacerbate frequently and usually last several days. Coughing and wheezing may disrupt normal daily activities and make it difficult to sleep. Nighttime symptom exacerbations occur more than once a week. In moderate asthma, lung function is roughly between 60% and 80% of normal, without treatment. The Global Initiative for Asthma (GINA) guidelines can be used to classify asthma severity, including moderate asthma.

In one example, the asthma is poorly controlled or uncontrolled asthma. The level of asthma control, as opposed to severity, can be determined using, for example, an Asthma Control Questionanaire (ACQ) as described in Juniper et al., (1999) Eur Respir J 14:902-907, Juniper et al., Respiratory Medicine (2006) 100:616-621, and Juniper et al., Respiratory Medicine (2005) 99:553-558.

In one example, the asthma is refractory asthma. As used herein, the term "refractory asthma" includes patients with "fatal" or "near fatal" asthma as well as the asthma subgroups such as "severe asthma" and "steroid-dependent and/or resistant asthma," "difficult to control asthma," "poorly controlled asthma," "brittle asthma," or "irreversible asthma." Refractory asthma can be defined as per the American Thoracic Society guidelines when one or both major criteria and two minor criteria, described as follows, are fulfilled. The major criteria are: In order to achieve control to a level of mild-moderate persistent asthma: (1) Treatment with continuous or near continuous (≥50% of year) oral corticosteroids 2) Requirement for treatment with high-dose inhaled corticosteroids. The minor criteria are: (1) Requirement for daily treatment with a controller medication in addition to inhaled corticosteroids e.g., LABA, theophylline or leukotriene antagonist (2) Asthma symptoms requiring short-acting β-agonist use on a daily or near daily basis (3) Persistent airway obstruction ($FEV_1$<80% predicted; diurnal peak expiratory flow (PEF) variability >20%) (4) One or more urgent care visits for asthma per year (5) Three or more oral steroid "bursts" per year (6) Prompt deterioration with ≤25% reduction in oral or inhaled corticosteroid dose (7) Near fatal asthma event in the past. For the purposes of definition of refractory asthma, the drug (μg/d) and the dose (puffs/d) are as follows: (a) Beclomethasone dipropionate>1,260>40 puffs (42 μg/inhalation) >20 puffs (84 μg/inhalation); (b) Budesonide>1,200>6 puffs; (c) Flunisolide>2,000>8 puffs; (d) Fluticasone propionate>880>8 puffs (110 μg), >4 puffs (220 μg); (e) Triamcinolone acetonide>2,000>20 puffs.

"Chronic asthma" is not caused by allergens, but rather a result of the inflammation obtained from acute asthma. Acute asthma causes chronic inflammation, which causes the mucosal epithelium to become hypersensitive to environmental responses. So simple environmental agents, such as smoke, can stimulate the hypersensitive epithelium to produce large amounts of mucous and constrict.

In one example, the subject is a human. In one example, the subject is an adult, for example over 18 years in age. In one example, the subject is a child, for example less than 18 years in age. In one example, the subject is between 5 and 35 years of age In one example, the subject is between 18 and 35 years of age. In one example, the subject does not have chronic obstructive pulmonary disease (COPD).

In one example, the subject has airway bacterial colonisation. Colonisation of potentially pathogenic bacteria in the airways is associated with an increased risk of developing severe asthma. Of significance, carriage of *Streptococcus pneumoniae* in the upper airways has been detected in around of 50% asthmatic children (Esposito et al., BMC Infect Dis, 2016. 16:12) and asthma is more common in children that were colonised with *S. pneumoniae, Moraxella catarrhalis* and/or *Haemophilus influenzae* during infancy. Methods for detecting and measuring bacterial colonisation of airways are known in the art. Suitable methods include culturing BAL fluid or lung tissue homogenates on horse blood agar plates to determine bacterial load, for example as described in (FitzPatrick et al., Sci Rep, 2016. 6:22751). Other methods include real time quantitative PCR on bacterial DNA isolated from lung tissue using a standard curve generated from a known quantity of bacteria.

In one example, the subject has a respiratory viral infection. In one example, the respiratory viral infection is an influenza virus infection. Respiratory viral infections may cause asthma symptoms to exacerbate and cause bacterial colonisation, if present, to disseminate into the lower airways of the subject. Accordingly, in one example, the subject has airway bacterial colonisation and a respiratory viral infection.

In some examples, the compound that inhibits G-CSF signaling is administered in an amount sufficient to reduce or prevent neutrophilic lung inflammation. As used herein, the term "neutrophilic lung inflammation" relates to any inflammatory response in the lung which is mediated by neutrophils. Neutrophilic inflammation is observed during asthma exacerbations and also in subgroups of patients with severe asthma that is more steroid-refractory. Neutrophilic inflammation, as opposed to eosinophilic inflammation, is typically characterised by upregulation of neutrophil chemotactic mediators such as CXCL1, infiltration of neutrophils in the airways, and neutrophil activation, resulting in release of cytotoxic products and the formation of neutrophil extracellular traps (NETs), or "NETosis". Methods for measuring neutrophilic lung inflammation are known in the art and include detecting the quantity of neutrophils in lung tissue or bronchoalveolar lavage by flow cytometry or immunohistochemistry (e.g., as described in Wang et al., Clin Sci Lond, 2017 131:2347-2362). Neutrophilic inflammation can also be assessed by detecting NETosis markers. For example, suitable methods include measuring neutrophil elastase activity on BAL fluid, for example by using an EnzChek™ Elastase Assay Kit. Content of double stranded DNA (dsDNA) in the BAL fluid can also be measured to assess neutrophilic inflammation using, for example, Quant-iT PicoGreen dsDNA reagent.

In one example, the compound that inhibits G-CSF signaling is administered in an amount sufficient to enhance lung function. Lung function can be assessed by, for example, spirometry. In one example, the compound that inhibits G-CSF signaling is administered in an amount sufficient to increase $FEV_1$ (forced expiratory volume in one second). In one example, the compound that inhibits G-CSF signaling is administered in an amount sufficient to increase FVC (forced vital capacity). The $FEV_1$ is the volume expired in the first second of maximal expiration initiated at full inspiration, and is one measure of lung function. FVC is the maximum volume of air that can be expired during the test.

In one example, the compound that inhibits G-CSF signaling is administered in an amount sufficient to reduce or prevent airway hyper-responsiveness (AHR). AHR is an increased sensitivity of the airways to an inhaled constrictor agonist, a steeper slope of the dose-response curve, and a greater maximal response to the agonist. AHR is generally associated with lower lung function and asthmatic symptoms. AHR can be assessed, for example, with a bronchial challenge test. This most often uses constrictor agonists like methacholine or histamine. These chemicals trigger bronchospasm in non-asthmatic subjects as well, but subjects with AHR have a lower response threshold to the constrictor agonists. Suitable methods are described in (FitzPatrick et al., Sci Rep, 2016 6:22751).

In one example, the compound that inhibits G-CSF signaling is administered in an amount sufficient to reduce or prevent an increase in mucus production. Increased production of mucus in the respiratory tract is a common effect of asthma, which leads to breathing difficulties and coughing. Furthermore, airway mucus plugging is frequently associated with death that results from asthma. Secretion of mucus from goblet cells also contributes to AHR in concert with airway smooth muscle contraction. Levels of mucus production can be estimated based on the volume and frequency of sputum produced by a subject. Levels of mucus production can also be assessed using histology techniques which are routine in the art, for example by staining with Alcian blue-periodic acid Schiff (AB-PAS) stain. Mucus production in the airways is also associated with expression of the mucin gene Muc5ac. Thus, mucus production can also be assessed by measuring Muc5ac expression by RT-PCR performed on lung tissue.

In one example, the compound that inhibits G-CSF signaling is administered in an amount sufficient to have one or more of the following effects in the subject's lung:
  (i) reduce or prevent an increase in neutrophil levels;
  (ii) reduce or prevent an increase in neutrophil elastase levels;
  (iii) reduce or prevent an increase in extracellular double stranded DNA levels;
  (iv) reduce or prevent an increase in eosinophil levels; and
  (v) reduce or prevent an increase in $T_H2$ cell levels.

Methods for assessing the above will be known in the art. For example, the levels of neutrophils, eosinophils, and $T_H2$ cells in lung tissue or bronchoalveolar lavage can be measured by flow cytometry or immunohistochemistry (e.g., as described in Wang et al., Clin Sci Lond, 2017 131:2347-2362). In particular, $T_H2$ cells (also known as Type 2 helper T cells) recruit and activate eosinophils and thus elevated levels of $T_H2$ cells in lung tissue is indicative of type 2 or eosinophilic inflammation in asthma. Neutrophil elastase levels can be assessed by measuring elastase activity in BAL fluid, for example by using an EnzChek™ Elastase Assay Kit. Content of extracellular double stranded DNA (dsDNA) in the BAL fluid, which is characteristic of neutrophilic inflammation, can be measured using, for example, Quant-iT PicoGreen dsDNA reagent.

In one example, the methods described herein further comprise identifying the subject as being responsive to treatment with a compound that inhibits G-CSF signaling. In one example, identifying the subject as being responsive to treatment with a compound that inhibits G-CSF signaling comprises determining that the subject has increased levels of neutrophils in sputum, for example greater than 40% or greater than 60% of sputum cells. In one example, identifying the subject as being responsive to treatment with a compound that inhibits G-CSF signaling comprises determining that the subject has increased expression of G-CSF and/or G-CSFR in bronchial biopsy tissue.

Antibodies

In one example, a compound as described herein according to any example is a protein comprising an antigen binding site of an antibody. In some examples, the compound that inhibits G-CSF signaling is an antibody. In some examples, the antibody binds to G-CSFR. In some examples, the antibody binds to G-CSF.

Methods for generating antibodies are known in the art and/or described in Harlow and Lane (editors) Antibodies: A Laboratory Manual, Cold Spring Harbor Laboratory, (1988). Generally, in such methods G-CSFR or G-CSF (e.g., hG-CSFR or hG-CSF) or a region thereof (e.g., an extracellular domain) or immunogenic fragment or epitope thereof or a cell expressing and displaying same (i.e., an immunogen), optionally formulated with any suitable or desired carrier, adjuvant, or pharmaceutically acceptable excipient, is administered to a non-human animal, for example, a mouse, chicken, rat, rabbit, guinea pig, dog, horse, cow, goat or pig. The immunogen may be administered intranasally, intramuscularly, sub-cutaneously, intravenously, intradermally, intraperitoneally, or by other known route.

Monoclonal antibodies are one exemplary form of an antibody contemplated by the present disclosure. The term "monoclonal antibody" or "mAb" refers to a homogeneous antibody population capable of binding to the same antigen(s), for example, to the same epitope within the antigen. This term is not intended to be limited as regards to the source of the antibody or the manner in which it is made.

For the production of mAbs any one of a number of known techniques may be used, such as, for example, the procedure exemplified in U.S. Pat. No. 4,196,265 or Harlow and Lane (1988), supra.

Alternatively, ABL-MYC technology (NeoClone, Madison WI 53713, USA) is used to produce cell lines secreting MAbs (e.g., as described in Largaespada et al, *J. Immunol. Methods*. 197: 85-95, 1996).

Antibodies can also be produced or isolated by screening a display library, e.g., a phage display library, e.g., as described in U.S. Pat. No. 6,300,064 and/or U.S. Pat. No. 5,885,793. For example, the present inventors have isolated fully human antibodies from a phage display library.

The antibody of the present disclosure may be a synthetic antibody. For example, the antibody is a chimeric antibody, a humanized antibody, a human antibody or a de-immunized antibody.

In one example, an antibody described herein is a chimeric antibody. The term "chimeric antibody" refers to antibodies in which a portion of the heavy and/or light chain is identical with or homologous to corresponding sequences in antibodies derived from a particular species (e.g., murine, such as mouse) or belonging to a particular antibody class or subclass, while the remainder of the chain(s) is identical with or homologous to corresponding sequences in antibodies derived from another species (e.g., primate, such as human) or belonging to another antibody class or subclass. Methods for producing chimeric antibodies are described in, e.g., US4816567; and U.S. Pat. No. 5,807,715.

The antibodies of the present disclosure may be humanized or human.

The term "humanized antibody" shall be understood to refer to a subclass of chimeric antibodies having an antigen binding site or variable region derived from an antibody from a non-human species and the remaining antibody structure based upon the structure and/or sequence of a human antibody. In a humanized antibody, the antigen-binding site generally comprises the complementarity determining regions (CDRs) from the non-human antibody grafted onto appropriate FRs in the variable regions of a human antibody and the remaining regions from a human antibody. Antigen binding sites may be wild-type (i.e., identical to those of the non-human antibody) or modified by one or more amino acid substitutions. In some instances, FR residues of the human antibody are replaced by corresponding non-human residues.

Methods for humanizing non-human antibodies or parts thereof (e.g., variable regions) are known in the art. Humanization can be performed following the method of U.S. Pat. No. 5,225,539, or U.S. Pat. No. 5,585,089. Other methods for humanizing an antibody are not excluded.

The term "human antibody" as used herein refers to antibodies having variable regions (e.g. $V_H$, $V_L$) and, optionally constant regions derived from or corresponding to sequences found in humans, e.g. in the human germline or somatic cells.

Exemplary human antibodies are described herein and include C1.2 and C1.2G and/or variable regions thereof. These human antibodies provide an advantage of reduced immunogenicity in a human compared to non-human antibodies. Exemplary antibodies are described in WO2012171057, which is incorporated herein by reference.
Antibody Binding Domain Containing Proteins
Single-Domain Antibodies In some examples, a compound of the disclosure is a protein that is or comprises a single-domain antibody (which is used interchangeably with the term "domain antibody" or "dAb"). A single-domain antibody is a single polypeptide chain comprising all or a portion of the heavy chain variable region of an antibody. In certain examples, a single-domain antibody is a human single-domain antibody (Domantis, Inc., Waltham, MA; see, e.g., U.S. Pat. No. 6,248,516).
Diabodies, Triabodies, Tetrabodies In some examples, a protein of the disclosure is or comprises a diabody, triabody, tetrabody or higher order protein complex such as those described in WO98/044001 and/or WO94/007921.
Single Chain Fv (scFv)

The skilled artisan will be aware that scFvs comprise $V_H$ and $V_L$ regions in a single polypeptide chain and a polypeptide linker between the $V_H$ and $V_L$ which enables the scFv to form the desired structure for antigen binding (i.e., for the $V_H$ and $V_L$ of the single polypeptide chain to associate with one another to form a Fv). For example, the linker comprises in excess of 12 amino acid residues with $(Gly_4Ser)_3$ being one of the more favored linkers for a scFv.
Heavy Chain Antibodies Heavy chain antibodies differ structurally from many other forms of antibodies, in so far as they comprise a heavy chain, but do not comprise a light chain. Accordingly, these antibodies are also referred to as "heavy chain only antibodies". Heavy chain antibodies are found in, for example, camelids and cartilaginous fish (also called IgNAR).

A general description of heavy chain antibodies from camelids and the variable regions thereof and methods for their production and/or isolation and/or use is found inter alia in the following references WO94/04678, WO97/49805 and WO 97/49805.

A general description of heavy chain antibodies from cartilaginous fish and the variable regions thereof and methods for their production and/or isolation and/or use is found inter alia in WO2005/118629.
Other Antibodies and Antibody Fragments The present disclosure also contemplates other antibodies and antibody fragments, such as:
(i) "key and hole" bispecific proteins as described in U.S. Pat. No. 5,731,168;
(ii) heteroconjugate proteins, e.g., as described in U.S. Pat. No. 4,676,980;
(iii) heteroconjugate proteins produced using a chemical cross-linker, e.g., as described in U.S. Pat. No. 4,676,980; and
(iv) $Fab_3$ (e.g., as described in EP19930302894).

V-Like Proteins

An example of a compound of the disclosure is a T-cell receptor. T cell receptors have two V-domains that combine into a structure similar to the Fv module of an antibody. Novotny et al., *Proc Natl Acad Sci USA* 88: 8646-8650, 1991 describes how the two V-domains of the T-cell receptor (termed alpha and beta) can be fused and expressed as a single chain polypeptide and, further, how to alter surface residues to reduce the hydrophobicity directly analogous to an antibody scFv. Other publications describing production of single-chain T-cell receptors or multimeric T cell receptors comprising two V-alpha and V-beta domains include WO1999/045110 or WO2011/107595.

Other non-antibody proteins comprising antigen binding domains include proteins with V-like domains, which are generally monomeric. Examples of proteins comprising such V-like domains include CTLA-4, CD28 and ICOS. Further disclosure of proteins comprising such V-like domains is included in WO1999/045110.

Adnectins

In one example, a compound of the disclosure is an adnectin. Adnectins are based on the tenth fibronectin type III ($^{10}$Fn3) domain of human fibronectin in which the loop regions are altered to confer antigen binding. For example, three loops at one end of the β-sandwich of the $^{10}$Fn3 domain can be engineered to enable an Adnectin to specifically recognize an antigen. For further details see US20080139791 or WO2005/056764.

Anticalins

In a further example, a compound of the disclosure is an anticalin. Anticalins are derived from lipocalins, which are a family of extracellular proteins which transport small hydrophobic molecules such as steroids, bilins, retinoids and lipids. Lipocalins have a rigid β-sheet secondary structure with a plurality of loops at the open end of the conical structure which can be engineered to bind to an antigen. Such engineered lipocalins are known as anticalins. For further description of anticalins see US7250297B1 or US20070224633.

Affibodies a further example, a compound of the disclosure is an affibody. An affibody is a scaffold derived from the Z domain (antigen binding domain) of Protein A of *phylococcus aureus* ch can be engineered to bind to antigen. The Z domain consists of a three-helical bundle of approximately 58 amino acids. Libraries have been generated by randomization of surface residues. For further details see EP1641818.

Avimers

In a further example, a compound of the disclosure is an Avimer. Avimers are multidomain proteins derived from the A-domain scaffold family. The native domains of approximately 35 amino acids adopt a defined disulfide bonded structure. Diversity is generated by shuffling of the natural variation exhibited by the family of A-domains. For further details see WO2002088171.

DARPins

In a further example, a compound of the disclosure is a Designed Ankyrin Repeat Protein (DARPin). DARPins are derived from Ankyrin which is a family of proteins that mediate attachment of integral membrane proteins to the cytoskeleton. A single ankyrin repeat is a 33 residue motif consisting of two α-helices and a β-turn. They can be engineered to bind different target antigens by randomizing residues in the first α-helix and a β-turn of each repeat. Their binding interface can be increased by increasing the number of modules (a method of affinity maturation). For further details see US20040132028.

Soluble G-CSFR

The present disclosure also contemplates a soluble form of the G-CSFR which competes with the naturally occurring membrane-associated G-CSFR for G-CSF interaction. Those skilled in the art can readily prepare soluble forms of the receptor, see for example U.S. Pat. No. 5,589,456 and Honjo et al, *Acta Crystallograph Sect F Struct Biol Cryst Commun.* 61(Pt 8):788-790, 2005.

De-Immunized Proteins

The present disclosure also contemplates a de-immunized antibody or protein.

De-immunized antibodies and proteins have one or more epitopes, e.g., B cell epitopes or T cell epitopes removed (i.e., mutated) to thereby reduce the likelihood that a mammal will raise an immune response against the antibody or protein. Methods for producing de-immunized antibodies and proteins are known in the art and described, for example, in WO2000/34317, WO2004/108158 and WO2004/064724.

Methods for introducing suitable mutations and expressing and assaying the resulting protein will be apparent to the skilled artisan based on the description herein.

Mutations to Proteins

The present disclosure also contemplates mutant forms of a protein of the disclosure. For example, such a mutant protein comprises one or more conservative amino acid substitutions compared to a sequence set forth herein. In some examples, the protein comprises 30 or fewer or 20 or fewer or 10 or fewer, e.g., 9 or 8 or 7 or 6 or 5 or 4 or 3 or 2 conservative amino acid substitutions. A "conservative amino acid substitution" is one in which the amino acid residue is replaced with an amino acid residue having a similar side chain and/or hydropathicity and/or hydrophilicity.

In one example, a mutant protein has only, or not more than, one or two or three or four or five or six conservative amino acid changes when compared to a naturally occurring protein. Details of conservative amino acid changes are provided below. As the skilled person would be aware, e.g., from the disclosure herein, such minor changes can reasonably be predicted not to alter the activity of the protein.

Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine).

The present disclosure also contemplates non-conservative amino acid changes (e.g., substitutions) in a protein of the present disclosure, e.g., in a CDR, such as CDR3. For example, the present inventors have identified several non-conservative amino acid substitutions that can be made while retaining an activity of a protein of the disclosure. In one example, the protein comprises fewer than 6 or 5 or 4 or 3 or 2 or 1 non-conservative amino acid substitutions, e.g., in a CDR3, such as in a CDR3.

The present disclosure also contemplates one or more insertions or deletions compared to a sequence set forth herein. In some examples, the protein comprises 10 or fewer, e.g., 9 or 8 or 7 or 6 or 5 or 4 or 3 or 2 insertions and/or deletions.

Constant Regions

The present disclosure encompasses proteins and/or antibodies described herein comprising a constant region of an antibody. This includes antigen binding fragments of an antibody fused to a Fc.

Sequences of constant regions useful for producing the proteins of the present disclosure may be obtained from a number of different sources. In some examples, the constant region or portion thereof of the protein is derived from a human antibody. The constant region or portion thereof may be derived from any antibody class, including IgM, IgG, IgD, IgA and IgE, and any antibody isotype, including IgG1, IgG2, IgG3 and IgG4. In one example, the constant region is human isotype IgG4 or a stabilized IgG4 constant region.

In one example, the Fc region of the constant region has a reduced ability to induce effector function, e.g., compared to a native or wild-type human IgG1 or IgG3 Fc region. In one example, the effector function is antibody-dependent cell-mediated cytotoxicity (ADCC) and/or antibody-dependent cell-mediated phagocytosis (ADCP) and/or complement-dependent cytotoxicity (CDC). Methods for assessing the level of effector function of an Fc region containing protein are known in the art and/or described herein.

In one example, the Fc region is an IgG4 Fc region (i.e., from an IgG4 constant region), e.g., a human IgG4 Fc region. Sequences of suitable IgG4 Fc regions will be apparent to the skilled person and/or available in publically available databases (e.g., available from National Center for Biotechnology Information).

In one example, the constant region is a stabilized IgG4 constant region. The term "stabilized IgG4 constant region" will be understood to mean an IgG4 constant region that has been modified to reduce Fab arm exchange or the propensity to undergo Fab arm exchange or formation of a half-antibody or a propensity to form a half antibody. "Fab arm exchange" refers to a type of protein modification for human IgG4, in which an IgG4 heavy chain and attached light chain (half-molecule) is swapped for a heavy-light chain pair from another IgG4 molecule. Thus, IgG4 molecules may acquire two distinct Fab arms recognizing two distinct antigens (resulting in bispecific molecules). Fab arm exchange occurs naturally in vivo and can be induced in vitro by purified blood cells or reducing agents such as reduced glutathione. A "half antibody" forms when an IgG4 antibody dissociates to form two molecules each containing a single heavy chain and a single light chain.

In one example, a stabilized IgG4 constant region comprises a proline at position 241 of the hinge region according to the system of Kabat (Kabat et al., Sequences of Proteins of Immunological Interest Washington DC United States Department of Health and Human Services, 1987 and/or 1991). This position corresponds to position 228 of the hinge region according to the EU numbering system (Kabat et al., Sequences of Proteins of Immunological Interest Washington DC United States Department of Health and Human Services, 2001 and Edelman et al., *Proc. Natl. Acad. USA,* 63, 78-85, 1969). In human IgG4, this residue is generally a serine. Following substitution of the serine for proline, the IgG4 hinge region comprises a sequence CPPC. In this regard, the skilled person will be aware that the "hinge region" is a proline-rich portion of an antibody heavy chain constant region that links the Fc and Fab regions that confers mobility on the two Fab arms of an antibody. The hinge region includes cysteine residues which are involved in inter-heavy chain disulfide bonds. It is generally defined as stretching from Glu226 to Pro243 of human IgG1 according to the numbering system of Kabat. Hinge regions of other IgG isotypes may be aligned with the IgG1 sequence by placing the first and last cysteine residues forming inter-heavy chain disulphide (S—S) bonds in the same positions (see for example WO2010/080538).

Additional examples of stabilized IgG4 antibodies are antibodies in which arginine at position 409 in a heavy chain constant region of human IgG4 (according to the EU numbering system) is substituted with lysine, threonine, methionine, or leucine (e.g., as described in WO2006/033386). The Fc region of the constant region may additionally or alternatively comprise a residue selected from the group consisting of: alanine, valine, glycine, isoleucine and leucine at the position corresponding to 405 (according to the EU numbering system). Optionally, the hinge region comprises a proline at position 241 (i.e., a CPPC sequence) (as described above).

In another example, the Fc region is a region modified to have reduced effector function, i.e., a "non-immunostimulatory Fc region". For example, the Fc region is an IgG1 Fc region comprising a substitution at one or more positions selected from the group consisting of 268, 309, 330 and 331. In another example, the Fc region is an IgG1 Fc region comprising one or more of the following changes E233P, L234V, L235A and deletion of G236 and/or one or more of the following changes A327G, A330S and P331S (Armour et al., *Eur J Immununol.* 29:2613-2624, 1999; Shields et al., *J Biol Chem.* 276(9):6591-604, 2001). Additional examples of non-immunostimulatory Fc regions are described, for example, in Dall'Acqua et al., *J Immununol.* 177: 1129-1138 2006; and/or Hezareh *J Virol;* 75: 12161-12168, 2001).

In another example, the Fc region is a chimeric Fc region, e.g., comprising at least one $C_H2$ domain from an IgG4 antibody and at least one $C_H3$ domain from an IgG1 antibody, wherein the Fc region comprises a substitution at one or more amino acid positions selected from the group consisting of 240, 262, 264, 266, 297, 299, 307, 309, 323, 399, 409 and 427 (EU numbering) (e.g., as described in WO2010/085682). Exemplary substitutions include 240F, 262L, 264T, 266F, 297Q, 299A, 299K, 307P, 309K, 309M, 309P, 323F, 399S, and 427F.

Additional Modifications

The present disclosure also contemplates additional modifications to an antibody or protein of the disclosure.

For example, the antibody comprises one or more amino acid substitutions that increase the half-life of the protein. For example, the antibody comprises a Fc region comprising one or more amino acid substitutions that increase the affinity of the Fc region for the neonatal Fc region (FcRn). For example, the Fc region has increased affinity for FcRn at lower pH, e.g., about pH 6.0, to facilitate Fc/FcRn binding in an endosome. In one example, the Fc region has increased affinity for FcRn at about pH 6 compared to its affinity at about pH 7.4, which facilitates the re-release of Fc into blood following cellular recycling. These amino acid substitutions are useful for extending the half life of a protein, by reducing clearance from the blood.

Exemplary amino acid substitutions include T250Q and/or M428L or T252A, T254S and T266F or M252Y, S254T and T256E or H433K and N434F according to the EU numbering system. Additional or alternative amino acid substitutions are described, for example, in US20070135620 or US7083784.

In one example, the protein of the disclosure additionally comprises albumin, a functional fragment or variant thereof. In one example, the albumin, functional fragment or variant thereof is serum albumin, such as human serum albumin. In one example, the albumin, functional fragment or variant thereof, comprises one or more amino acid substitutions, deletions or insertions, e.g., no more than 5 or 4 or 3 or 2 or 1 substitutions. Amino acid substitutions suitable for use in the present disclosure will be apparent to the skilled person and include naturally-occurring substitutions and engineered substitutions such as those described, for example, in WO2011051489, WO2014072481, WO2011103076, WO2012112188, WO2013075066, WO2015063611 and WO2014179657.

Protein Production

In one example, a protein described herein according to any example is produced by culturing a hybridoma under conditions sufficient to produce the protein, e.g., as described herein and/or as is known in the art.

Recombinant Expression

In another example, a protein described herein according to any example is recombinant.

In the case of a recombinant protein, nucleic acid encoding same can be cloned into expression constructs or vectors, which are then transfected into host cells, such as *E. coli* cells, yeast cells, insect cells, or mammalian cells, such as simian COS cells, Chinese Hamster Ovary (CHO) cells, human embryonic kidney (HEK) cells, or myeloma cells that do not otherwise produce the protein. Exemplary cells used for expressing a protein are CHO cells, myeloma cells or HEK cells. Molecular cloning techniques to achieve these ends are known in the art and described, for example in Ausubel et al., (editors), Current Protocols in Molecular Biology, Greene Pub. Associates and Wiley-Interscience (1988, including all updates until present) or Sambrook et al., Molecular Cloning: A Laboratory Manual, Cold Spring Harbor Laboratory Press (1989). A wide variety of cloning and in vitro amplification methods are suitable for the construction of recombinant nucleic acids. Methods of producing recombinant antibodies are also known in the art, see, e.g., U.S. Pat. No. 4,816,567 or U.S. Pat. No. 5,530,101.

Following isolation, the nucleic acid is inserted operably linked to a promoter in an expression construct or expression vector for further cloning (amplification of the DNA) or for expression in a cell-free system or in cells.

As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid, e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid to which it is operably linked. Exemplary promoters can contain additional copies of one or more specific regulatory elements to further enhance expression and/or alter the spatial expression and/or temporal expression of said nucleic acid.

As used herein, the term "operably linked to" means positioning a promoter relative to a nucleic acid such that expression of the nucleic acid is controlled by the promoter.

Many vectors for expression in cells are available. The vector components generally include, but are not limited to, one or more of the following: a signal sequence, a sequence encoding a protein (e.g., derived from the information provided herein), an enhancer element, a promoter, and a transcription termination sequence. The skilled artisan will be aware of suitable sequences for expression of a protein. Exemplary signal sequences include prokaryotic secretion signals (e.g., pelB, alkaline phosphatase, penicillinase, Ipp, or heat-stable enterotoxin II), yeast secretion signals (e.g., invertase leader, α factor leader, or acid phosphatase leader) or mammalian secretion signals (e.g., herpes simplex gD signal).

Exemplary promoters active in mammalian cells include cytomegalovirus immediate early promoter (CMV-IE), human elongation factor 1-α promoter (EF1), small nuclear RNA promoters (U1a and U1b), α-myosin heavy chain promoter, Simian virus 40 promoter (SV40), Rous sarcoma virus promoter (RSV), Adenovirus major late promoter, β-actin promoter; hybrid regulatory element comprising a CMV enhancer/β-actin promoter or an immunoglobulin promoter or active fragment thereof. Examples of useful mammalian host cell lines are monkey kidney CV1 line transformed by SV40 (COS-7, ATCC CRL 1651); human embryonic kidney line (293 or 293 cells subcloned for growth in suspension culture; baby hamster kidney cells (BHK, ATCC CCL 10); or Chinese hamster ovary cells (CHO).

Typical promoters suitable for expression in yeast cells such as for example a yeast cell selected from the group comprising *Pichia pastoris, Saccharomyces cerevisiae* and *S. pombe*, include, but are not limited to, the ADH1 promoter, the GAL1 promoter, the GAL4 promoter, the CUP1 promoter, the PHO5 promoter, the nmt promoter, the RPR1 promoter, or the TEF1 promoter.

Means for introducing the isolated nucleic acid or expression construct comprising same into a cell for expression are known to those skilled in the art. The technique used for a given cell depends on the known successful techniques. Means for introducing recombinant DNA into cells include microinjection, transfection mediated by DEAE-dextran, transfection mediated by liposomes such as by using lipofectamine (Gibco, MD, USA) and/or cellfectin (Gibco, MD, USA), PEG-mediated DNA uptake, electroporation and microparticle bombardment such as by using DNA-coated tungsten or gold particles (Agracetus Inc., WI, USA) amongst others.

The host cells used to produce the protein may be cultured in a variety of media, depending on the cell type used. Commercially available media such as Ham's F10 (Sigma), Minimal Essential Medium ((MEM), (Sigma), RPM1-1640 (Sigma), and Dulbecco's Modified Eagle's Medium ((DMEM), Sigma) are suitable for culturing mammalian cells. Media for culturing other cell types discussed herein are known in the art.

Isolation of Proteins

Methods for isolating a protein are known in the art and/or described herein.

Where a protein is secreted into culture medium, supernatants from such expression systems can be first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants. Alternatively, or additionally, supernatants can be filtered and/or separated from cells expressing the protein, e.g., using continuous centrifugation.

The protein prepared from the cells can be purified using, for example, ion exchange, hydroxyapatite chromatography, hydrophobic interaction chromatography, gel electrophoresis, dialysis, affinity chromatography (e.g., protein A affinity chromatography or protein G chromatography), or any combination of the foregoing. These methods are known in the art and described, for example in WO99/57134 or Ed Harlow and David Lane (editors) Antibodies: A Laboratory Manual, Cold Spring Harbor Laboratory, (1988).

The skilled artisan will also be aware that a protein can be modified to include a tag to facilitate purification or detection, e.g., a poly-histidine tag, e.g., a hexa-histidine tag, or a influenza virus hemagglutinin (HA) tag, or a Simian Virus 5 (V5) tag, or a FLAG tag, or a glutathione S-transferase (GST) tag. The resulting protein is then purified using methods known in the art, such as, affinity purification. For example, a protein comprising a hexa-his tag is purified by contacting a sample comprising the protein with nickelnitrilotriacetic acid (Ni-NTA) that specifically binds a hexa-his tag immobilized on a solid or semi-solid support, washing the sample to remove unbound protein, and subsequently eluting the bound protein. Alternatively, or in addition a ligand or antibody that binds to a tag is used in an affinity purification method.

Nucleic Acid-Based G-CSF Signaling Inhibitors

In one example of the disclosure, therapeutic and/or prophylactic methods as described herein according to any example of the disclosure involve reducing expression of G-CSF and/or G-CSFR. For example, such a method involves administering a compound that reduces transcription and/or translation of a nucleic acid encoding G-CSF or G-CSFR. In one example, the compound that inhibits G-CSF signaling is a nucleic acid, e.g., an antisense polynucleotide, a ribozyme, a PNA, an interfering RNA, a siRNA, a microRNA.

In another example, the compound that inhibits G-CSF signaling is a nucleic acid encoding a protein compound that inhibits G-CSF signaling (e.g., an antibody or antigen binding fragment thereof).

Antisense Nucleic Acids

The term "antisense nucleic acid" shall be taken to mean a DNA or RNA or derivative thereof (e.g., LNA or PNA), or combination thereof that is complementary to at least a portion of a specific mRNA molecule encoding a polypeptide as described herein in any example of the disclosure and capable of interfering with a post-transcriptional event such as mRNA translation. The use of antisense methods is known in the art (see for example, Hartmann and Endres (editors), Manual of Antisense Methodology, Kluwer (1999)).

An antisense nucleic acid of the disclosure will hybridize to a target nucleic acid under physiological conditions. Antisense nucleic acids include sequences that correspond to structural genes or coding regions or to sequences that effect control over gene expression or splicing. For example, the antisense nucleic acid may correspond to the targeted coding region of a nucleic acid encoding G-CSF or G-CSFR, or the 5'-untranslated region (UTR) or the 3'-UTR or combination of these. It may be complementary in part to intron sequences, which may be spliced out during or after transcription, for example only to exon sequences of the target gene. The length of the antisense sequence should be at least 19 contiguous nucleotides, for example, at least 50 nucleotides, such as at least 100, 200, 500 or 1000 nucleotides of a nucleic acid encoding G-CSF or G-CSFR. The full-length sequence complementary to the entire gene transcript may be used. The length can be 100-2000 nucleotides. The degree of identity of the antisense sequence to the targeted transcript should be at least 90%, for example, 95-100%.

Exemplary antisense nucleic acids against G-CSF or G-CSFR are described, for example, in WO2011032204.

Catalytic Nucleic Acid

The term "catalytic nucleic acid" refers to a DNA molecule or DNA-containing molecule (also known in the art as a "deoxyribozyme" or "DNAzyme") or a RNA or RNA-containing molecule (also known as a "ribozyme" or "RNAzyme") which specifically recognizes a distinct substrate and catalyzes the chemical modification of this substrate. The nucleic acid bases in the catalytic nucleic acid can be bases A, C, G, T (and U for RNA).

Typically, the catalytic nucleic acid contains an antisense sequence for specific recognition of a target nucleic acid, and a nucleic acid cleaving enzymatic activity (also referred to herein as the "catalytic domain"). The types of ribozymes that are useful in this disclosure are a hammerhead ribozyme and a hairpin ribozyme.

RNA Interference

RNA interference (RNAi) is useful for specifically inhibiting the production of a particular protein. Without being limited by theory, this technology relies on the presence of dsRNA molecules that contain a sequence that is essentially identical to the mRNA of the gene of interest or part thereof, in this case an mRNA encoding G-CSF or G-CSFR. Conveniently, the dsRNA can be produced from a single promoter in a recombinant vector host cell, where the sense and anti-sense sequences are flanked by an unrelated sequence which enables the sense and anti-sense sequences to hybridize to form the dsRNA molecule with the unrelated sequence forming a loop structure. The design and production of suitable dsRNA molecules for the present disclosure is well within the capacity of a person skilled in the art, particularly considering WO99/32619, WO99/53050, WO99/49029, and WO01/34815. Such dsRNA molecules for RNAi include, but are not limited to short hairpin RNA (shRNA) and bi-functional shRNA.

The length of the sense and antisense sequences that hybridize should each be at least 19 contiguous nucleotides, such as at least 30 or 50 nucleotides, for example at least 100, 200, 500 or 1000 nucleotides. The full-length sequence corresponding to the entire gene transcript may be used. The lengths can be 100-2000 nucleotides. The degree of identity of the sense and antisense sequences to the targeted transcript should be at least 85%, for example, at least 90% such as, 95-100%.

Exemplary small interfering RNA ("siRNA") molecules comprise a nucleotide sequence that is identical to about 19-21 contiguous nucleotides of the target mRNA. For example, the siRNA sequence commences with the dinucleotide AA, comprises a GC-content of about 30-70% (for example, 30-60%, such as 40-60% for example about 45%-55%), and does not have a high percentage identity to any nucleotide sequence other than the target in the genome of the mammal in which it is to be introduced, for example as determined by standard BLAST search.

Aptamers

In another example, a compound is a nucleic acid aptamer (adaptable oligomer). Aptamers are single stranded oligonucleotides or oligonucleotide analogs that are capable of forming a secondary and/or tertiary structure that provides the ability to bind to a particular target molecule, such as a protein or a small molecule, e.g., G-CSF or G-CSFR. Thus, aptamers are the oligonucleotide analogy to antibodies. In general, aptamers comprise about 15 to about 100 nucleotides, such as about 15 to about 40 nucleotides, for example about 20 to about 40 nucleotides, since oligonucleotides of a length that falls within these ranges can be prepared by conventional techniques.

An aptamer can be isolated from or identified from a library of aptamers. An aptamer library is produced, for example, by cloning random oligonucleotides into a vector (or an expression vector in the case of an RNA aptamer), wherein the random sequence is flanked by known sequences that provide the site of binding for PCR primers. An aptamer that provides the desired biological activity (e.g., binds specifically to G-CSF or G-CSFR) is selected. An aptamer with increased activity is selected, for example, using SELEX (Sytematic Evolution of Ligands by EXponential enrichment). Suitable methods for producing and/or screening an aptamer library are described, for example, in Ellloington and Szostak, *Nature* 346:818-22, 1990; U.S. Pat. No. 5,270,163; and/or U.S. Pat. No. 5,475,096.

Assaying Activity of a Compound Binding to G-CSFR and Mutants Thereof

It will be apparent to the skilled artisan from the disclosure herein that some compounds of the present disclosure bind to the ligand binding domain of hG-CSFR and to specific mutant forms of the ligand binding domain of hG-CSFR (e.g., SEQ ID NO: 1 without or with certain point mutations) and/or bind to both human and cynomolgus monkey G-CSFR. Methods for assessing binding to a protein are known in the art, e.g., as described in Scopes (In: Protein purification: principles and practice, Third Edition, Springer Verlag, 1994). Such a method generally involves labeling the protein and contacting it with immobilized compound. Following washing to remove non-specific bound protein, the amount of label and, as a consequence, bound protein is detected. Of course, the protein can be immobilized and the compound that inhibits G-CSF signaling labeled. Panning-type assays can also be used. Alternatively, or additionally, surface plasmon resonance assays can be used.

The assays described above can also be used to detect the level of binding of a compound to hG-CSFR or a ligand binding domain thereof (e.g., SEQ ID NO: 1) or mutant form thereof.

In one example, a protein of the present disclosure binds to a polypeptide of SEQ ID NO: 1 in which an alanine is substituted for the lysine at position 167 of SEQ ID NO: 1 and/or in which an alanine is substituted for the histidine at position 168 of SEQ ID NO: 1 at substantially the same level (e.g., within 10% or 5% or 1%) as it binds to SEQ ID NO: 1.

In one example, a protein of the present disclosure binds to a polypeptide of SEQ ID NO: 1 in which an alanine is substituted for the arginine at position 287 of SEQ ID NO: 1 at a level at least about 100 fold or 150 fold or 160 fold or 200 fold lower than it binds to a polypeptide of SEQ ID NO: 1. In one example, a protein of the present disclosure binds to a polypeptide of SEQ ID NO: 1 in which an alanine is substituted for the arginine at position 287 of SEQ ID NO: 1 at a level at least about 160 fold lower than it binds to a polypeptide of SEQ ID NO: 1.

In one example, a protein of the present disclosure binds to a polypeptide of SEQ ID NO: 1 in which an alanine is substituted for the histidine at position 237 of SEQ ID NO: 1 at a level at least about 20 fold or 40 fold or 50 fold or 60 fold lower than it binds to a polypeptide of SEQ ID NO: 1. In one example, a protein of the present disclosure binds to a polypeptide of SEQ ID NO: 1 in which an alanine is substituted for the histidine at position 237 of SEQ ID NO: 1 at a level at least about 50 fold lower than it binds to a polypeptide of SEQ ID NO: 1.

In one example, a protein of the present disclosure binds to a polypeptide of SEQ ID NO: 1 in which an alanine is substituted for the methionine at position 198 of SEQ ID NO: 1 at a level at least about 20 fold or 40 fold or 60 fold or 70 fold lower than it binds to a polypeptide of SEQ ID NO: 1. In one example, a protein of the present disclosure binds to a polypeptide of SEQ ID NO: 1 in which an alanine is substituted for the methionine at position 198 of SEQ ID NO: 1 at a level at least about 40 fold lower than it binds to a polypeptide of SEQ ID NO: 1.

In one example, a protein of the present disclosure binds to a polypeptide of SEQ ID NO: 1 in which an alanine is substituted for the tyrosine at position 172 of SEQ ID NO: 1 at a level at least about 20 fold or 30 fold or 40 fold lower than it binds to a polypeptide of SEQ ID NO: 1. In one example, a protein of the present disclosure binds to a polypeptide of SEQ ID NO: 1 in which an alanine is substituted for the tyrosine at position 172 of SEQ ID NO: 1 at a level at least about 40 fold lower than it binds to a polypeptide of SEQ ID NO: 1.

In one example, a protein of the present disclosure binds to a polypeptide of SEQ ID NO: 1 in which an alanine is substituted for the leucine at position 171 of SEQ ID NO: 1 at a level at least about 100 fold or 120 fold or 130 fold or 140 fold lower than it binds to a polypeptide of SEQ ID NO: 1. In one example, a protein of the present disclosure binds to a polypeptide of SEQ ID NO: 1 in which an alanine is substituted for the leucine at position 171 of SEQ ID NO: 1 at a level at least about 140 fold lower than it binds to a polypeptide of SEQ ID NO: 1.

In one example, a protein of the present disclosure binds to a polypeptide of SEQ ID NO: 1 in which an alanine is substituted for the leucine at a position 111 of SEQ ID NO: 1 at a level at least about 20 fold or 40 fold or 60 fold or 70 fold lower than it binds to a polypeptide of SEQ ID NO: 1. In one example, a protein of the present disclosure binds to a polypeptide of SEQ ID NO: 1 in which an alanine is substituted for the leucine at a position 111 of SEQ ID NO: 1 at a level at least about 60 fold lower than it binds to a polypeptide of SEQ ID NO: 1.

In one example, a protein of the present disclosure binds to a polypeptide of SEQ ID NO: 1 in which an alanine is substituted for the histidine at position 168 of SEQ ID NO: 1 at a level no more than 5 fold or 4 fold or 3 fold or 2 fold or 1 fold lower than it binds to a polypeptide of SEQ ID NO: 1.

In one example, a protein of the present disclosure binds to a polypeptide of SEQ ID NO: 1 in which an alanine is substituted for the lysine at position 167 of SEQ ID NO: 1 at a level no more than 5 fold or 4 fold or 3 fold or 2 fold or 1 fold lower than it binds to a polypeptide of SEQ ID NO: 1.

The level of binding is conveniently determined using a biosensor.

The present disclosure contemplates any combination of the foregoing characteristics. In one example, a protein described herein has all of the binding characteristics set forth in the preceding seven paragraphs.

Epitope Mapping

In another example, the epitope bound by a protein described herein is mapped. Epitope mapping methods will be apparent to the skilled artisan. For example, a series of overlapping peptides spanning the hG-CSFR sequence or a region thereof comprising an epitope of interest, e.g., peptides comprising 10-15 amino acids are produced. The protein is then contacted to each peptide and the peptide(s) to which it binds determined. This permits determination of peptide(s) comprising the epitope to which the protein binds. If multiple non-contiguous peptides are bound by the protein, the protein may bind a conformational epitope.

Alternatively, or in addition, amino acid residues within hG-CSFR are mutated, e.g., by alanine scanning mutagenesis, and mutations that reduce or prevent protein binding are determined. Any mutation that reduces or prevents binding of the protein is likely to be within the epitope bound by the protein.

A further method is exemplified herein, and involves binding hG-CSFR or a region thereof to an immobilized protein of the present disclosure and digesting the resulting complex with proteases. Peptide that remains bound to the immobilized protein are then isolated and analyzed, e.g., using mass spectrometry, to determine their sequence.

A further method involves converting hydrogens in hG-CSFR or a region thereof to deutrons and binding the resulting protein to an immobilized protein of the present disclosure. The deutrons are then converted back to hydrogen, the hG-CSFR or region thereof isolated, digested with enzymes and analyzed, e.g., using mass spectrometry to identify those regions comprising deutrons, which would have been protected from conversion to hydrogen by the binding of a protein described herein.

Optionally, the dissociation constant (Kd) of a protein for hG-CSFR or an epitope thereof is determined. The "Kd" or "Kd value" for a hG-CSFR binding protein is in one example measured by a radiolabeled or fluorescently-labeled hG-CSFR binding assay. This assay equilibrates the protein with a minimal concentration of labeled G-CSFR in the presence of a titration series of unlabeled hG-CSFR. Following washing to remove unbound hG-CSFR, the amount of label is determined, which is indicative of the Kd of the protein.

According to another example the Kd or Kd value is measured by using surface plasmon resonance assays, e.g., using BIAcore surface plasmon resonance (BIAcore, Inc., Piscataway, NJ) with immobilized hG-CSFR or a region thereof.

In some examples, proteins having a similar Kd or a higher Kd than C1.2 or C1.2G are selected, because they are likely to compete for binding to hG-CSFR.

Determining Competitive Binding

Assays for determining a protein that competitively inhibits its binding of monoclonal antibody C1.2 or C1.2G will be apparent to the skilled artisan. For example, C1.2 or C1.2G is conjugated to a detectable label, e.g., a fluorescent label or a radioactive label. The labeled antibody and the test protein are then mixed and contacted with hG-CSFR or a region thereof (e.g., a polypeptide comprising SEQ ID NO: 1) or a cell expressing same. The level of labeled C1.2 or C1.2G is then determined and compared to the level determined when the labeled antibody is contacted with the hG-CSFR, region or cells in the absence of the protein. If the level of labeled C1.2 or C1.2G is reduced in the presence of the test protein compared to the absence of the protein, the protein is considered to competitively inhibit binding of C1.2 or C1.2G to hG-CSFR.

Optionally, the test protein is conjugated to different label to C1.2 or C1.2G. This alternate labeling permits detection of the level of binding of the test protein to hG-CSFR or the region thereof or the cell.

In another example, the protein is permitted to bind to hG-CSFR or a region thereof (e.g., a polypeptide comprising SEQ ID NO: 1) or a cell expressing same prior to contacting the hG-CSFR, region or cell with C1.2 or C1.2G. A reduction in the amount of bound C1.2 or C1.2G in the presence of the protein compared to in the absence of the protein indicates that the protein competitively inhibits C1.2 or C1.2G binding to hG-CSFR. A reciprocal assay can also be performed using labeled protein and first allowing C1.2 or C1.2G to bind to G-CSFR. In this case, a reduced amount of labeled protein bound to hG-CSFR in the presence of C1.2 or C1.2G compared to in the absence of C1.2 or C1.2G indicates that the protein competitively inhibits binding of C1.2 or C1.2G to hG-CSFR.

Any of the foregoing assays can be performed with a mutant form of hG-CSFR and/or SEQ ID NO: 1 and/or a ligand binding region of hG-CSFR to which C1.2 or C1.2G binds, e.g., as described herein.

Determining Inhibition of G-CSF Signaling

In some examples of the present disclosure, a compound is capable of neutralizing hG-CSFR signaling.

Various assays are known in the art for assessing the ability of a compound to neutralize signaling of a ligand through a receptor.

In one example, the compound that inhibits G-CSF signaling reduces or prevents G-CSF binding to the hG-CSFR. These assays can be performed as a competitive binding assay as described herein using labeled G-CSF and/or labeled protein.

In another example, the compound that inhibits G-CSF signaling reduces formation of CFU-G when $CD34^+$ bone marrow cells are cultured in the presence of G-CSF. In such assays, $CD34^+$ bone marrow cells are cultured in a semi-solid cell culture medium in the presence of G-CSF (e.g., about lOng/ml cell culture medium) and, optionally stem cell factor (e.g., about lOng/ml cell culture medium) in the presence or absence of a test compound. After a sufficient time for granulocyte clones (CFU-G) to form, the number of clones or colonies is determined. A reduction in the number of colonies in the presence of the compound that inhibits G-CSF signaling compared to in the absence of the compound that inhibits G-CSF signaling indicates that the compound that inhibits G-CSF signaling neutralizes G-CSF signaling. By testing multiple concentrations of the compound that inhibits G-CSF signaling an IC50 is determined, i.e., a concentration at which 50% of the maximum inhibition of CFU-G formation occurs. In one example, the $IC_{50}$ is 0.2 nM or less, such as 0.1 nM or less, for example, 0.09 nM or less, or 0.08 nM or less, or 0.07 nM or less, or 0.06 nM or less or0.05 nM or less. In one example, the $IC_{50}$ is 0.04 nM or less. In another example, the $IC_{50}$ is 0.02 nM or less. The foregoing ICsos relate to any CFU-G assay described herein.

In a further example, the compound that inhibits G-CSF signaling reduces proliferation of cells (e.g., BaF3 cells) expressing hG-CSFR which are cultured in the presence of G-CSF. Cells are cultured in the presence of G-CSF (e.g., 0.5 ng/ml) and the presence or absence of a test compound. Methods for assessing cell proliferation are known in the art and include, for example, MTT reduction and thymidine incorporation. A compound that reduces the level of proliferation compared to the level observed in the absence of the compound is considered to neutralize G-CSF signaling. By testing multiple concentrations of the compound an $IC_{50}$ is determined, i.e., a concentration at which 50% of the maximum inhibition of cell proliferation occurs. In one example, the $IC_{50}$ is 6 nM or less, such as 5.9 nM or less. In another example, the $IC_{50}$ is 2 nM or less or 1 nM or less or 0.7 nM or cell or 0.6 nM or less or 0.5 nM or less. The foregoing $IC_{50}$s relate to any cell proliferation assay described herein.

In a further example, the compound that inhibits G-CSF signaling reduces mobilization of hematopoietic stem cells and/or endothelial progenitor cells in vivo following G-CSF administration and/or reduces the number of neutrophils in vivo, e.g., following G-CSF administration (however this is not essential). For example, the compound that inhibits G-CSF signaling is administered, optionally before, at the time of or after administration of G-CSF or a modified form thereof (e.g., PEGylated G-CSF or filgrastim). The number of hematopoietic stem cells (e.g., expressing CD34 and/or Thy1) and/or endothelial progenitor cells (e.g., expressing CD34 and VEGFR2) and/or neutrophils (identified morphologically and/or expressing e.g., CD10, CD14, CD31 and/or CD88) is assessed. A compound that reduces the level of the cell(s) compared to the level observed in the absence of the compound is considered to neutralize G-CSF signaling. In one example, the compound that inhibits G-CSF signaling reduces the number of neutrophils without inducing neutropenia.

Other methods for assessing neutralization of G-CSF signaling are contemplated by the present disclosure.

Determining Effector Function

As discussed herein, some proteins of the present disclosure have reduced effector function. Methods for assessing ADCC activity are known in the art.

In one example, the level of ADCC activity is assessed using a $^{51}$Cr release assay, an europium release assay or a $^{35}$S release assay. In each of these assays, cells expressing G-CSFR are cultured with one or more of the recited compounds that inhibit G-CSF signaling for a time and under conditions sufficient for the compound to be taken up by the cell. In the case of a $^{35}$S release assay, cells expressing hG-CSFR can be cultured with $^{35}$S-labeled methionine and/or cysteine for a time sufficient for the labeled amino acids to be incorporated into newly synthesized proteins. Cells are then cultured in the presence or absence of the protein and in the presence of immune effector cells, e.g., peripheral blood mononuclear cells (PBMC) and/or NK cells. The amount of $^{51}$Cr, europium and/or $^{35}$S in cell culture medium is then detected, and little or no change in the presence of the protein compared to in the absence of protein (or a reduced level of the compound compared to the level observed in the presence of an anti-hG-CSFR antibody comprising a human IgG1 Fc) indicates that the protein has reduced effector function. Exemplary publications disclosing assays for assessing the level of ADCC induced by a protein include Hellstrom, et al. *Proc. Natl Acad. Sci. USA* 83:7059-7063, 1986 and Bruggemann, et al., *J. Exp. Med.* 166:1351-1361, 1987.

Other assays for assessing the level of ADCC induced by a protein include ACTI™ nonradioactive cytotoxicity assay for flow cytometry (CellTechnology, Inc. CA, USA) or CytoTox 96® non-radioactive cytotoxicity assay (Promega, WI, USA).

C1q binding assays may also be carried out to confirm that the protein is able to bind C1q and may induce CDC. To assess complement activation, a CDC assay may be performed (see, for example, Gazzano-Santoro et al, *J. Immunol. Methods* 202: 163, 1996.

Determining Half Life

Some proteins encompassed by the present disclosure have an improved half-life, e.g., are modified to extend their half-life compared to proteins that are unmodified. Methods for determining a protein with an improved half-life will be apparent to the skilled person. For example, the ability of a protein to bind to a neonatal Fc receptor (FcRn) is assessed. In this regard, increased binding affinity for FcRn increased the serum half-life of the molecule (see for example, Kim et al., *Eur J Immunol.*, 24:2429, 1994).

The half-life of a protein of the disclosure can also be measured by pharmacokinetic studies, e.g., according to the method described by Kim et al, *Eur J of Immunol* 24:542, 1994. According to this method radiolabeled protein is injected intravenously into mice and its plasma concentration is periodically measured as a function of time, for example at 3 minutes to 72 hours after the injection. The clearance curve thus obtained should be biphasic, that is, an alpha phase and beta phase. For the determination of the in vivo half-life of the protein, the clearance rate in beta-phase is calculated and compared with that of the wild type or unmodified protein.

Therapeutic Efficacy

The therapeutic efficacy of a compound that inhibits G-CSF signaling may be assessed in an animal model. Exemplary models of respiratory conditions include an animal model of allergy, e.g., allergic asthma, such as a model described in WO2002/098216, a mouse model of allergic asthma, e.g., induced by host dust mite protein (Fattouh et al., *Am J Respir Crit Care Med* 172: 314-321, 2005), a mouse model of severe asthma in which IL-5 and eotaxin are overexpressed, mice receiving intratracheal instillation of poly-1-lysine which are hypersensitive to methacholine when delivered as an aerosol (Homma et al., *Am J Physiol Lung Cell Mol Physiol* 289: L413-L418, 2005), bleomycin or FITC or silica induced models of pulmonary fibrosis (Muggia et al., *Cancer Treat Rev* 10: 221-243, 1983; Roberts et al., *J Pathol* 176: 309-318, 1995; Oberdorster Inhal Toxicol 8: 73-89, 1996).

The ability of a compound that inhibits G-CSF signaling to prevent or reduce the severity of an asthma exacerbation can also be assessed in an animal model. For example, a model of allergic asthma using mice exposed to house dust mite, in which exacerbation is induced by infection with bacteria (e.g., *eptococcus pneumoniae* and/or a virus (e.g., influenza virus). A number of other animal models for assessing preventing or reducing severity of an asthma exacerbation are described in Kumar et al., *Respirology* (2016) 21:842-9.

Compositions

In some examples, a compound as described herein can be administered orally, parenterally, by inhalation spray, adsorption, absorption, topically, rectally, nasally, bucally, vaginally, intraventricularly, via an implanted reservoir in dosage formulations containing conventional non-toxic pharmaceutically-acceptable carriers, or by any other convenient dosage form. The term "parenteral" as used herein includes subcutaneous, intravenous, intramuscular, intraperitoneal, intrathecal, intraventricular, intrasternal, and intracranial injection or infusion techniques.

Methods for preparing a compound into a suitable form for administration (e.g. a pharmaceutical composition) are known in the art and include, for example, methods as described in Remington's Pharmaceutical Sciences (18th ed., Mack Publishing Co., Easton, Pa., 1990) and U.S. Pharmacopeia: National Formulary (Mack Publishing Company, Easton, Pa., 1984).

The pharmaceutical compositions of this disclosure are particularly useful for parenteral administration, such as intravenous administration or subcutaneous administration or administration into a body cavity or lumen of an organ or joint. The compositions for administration will commonly comprise a solution of the compound that inhibits G-CSF signaling dissolved in a pharmaceutically acceptable carrier, for example an aqueous carrier. A variety of aqueous carriers can be used, e.g., buffered saline and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of compound of the present disclosure in these formulations can vary widely, and will be selected primarily based on fluid volumes, viscosities, body weight and the like in accordance with the particular mode of administration selected and the patient's needs. Exemplary carriers include water, saline, Ringer's solution, dextrose solution, and 5% human serum albumin. Nonaqueous vehicles such as mixed oils and ethyl oleate may also be used. Liposomes may also be used as carriers. The vehicles may contain minor amounts of additives that enhance isotonicity and chemical stability, e.g., buffers and preservatives.

Upon formulation, compounds of the present disclosure will be administered in a manner compatible with the dosage formulation and in such amount as is therapeutically/prophylactically effective. Formulations are easily administered in a variety of dosage forms, such as the type of injectable solutions described above, but other pharmaceutically acceptable forms are also contemplated, e.g., tablets, pills, capsules or other solids for oral administration, suppositories, pessaries, nasal solutions or sprays, aerosols, inhalants, liposomal forms and the like. Pharmaceutical "slow release" capsules or compositions may also be used. Slow release formulations are generally designed to give a constant drug level over an extended period and may be used to deliver compounds of the present disclosure.

WO2002/080967 describes compositions and methods for administering aerosolized compositions comprising antibodies for the treatment of asthma, which are also suitable for administration of a compound of the present disclosure.

Combination Therapies

In one example, a compound of the present disclosure is administered in combination with another compound useful for treating a disease or condition described herein, either as combined or additional treatment steps or as additional components of a therapeutic formulation.

In some examples, the other compound is one that is commonly used to treat asthma. For example, the other compound can be an anti-inflammatory compound. Alternatively, or additionally, the other compound is an immunomodulatory or an immunosuppressant. Alternatively, or additionally, the other compound is a corticosteroid, such as a glucocorticoid, beclometasone, budesonide, ciclesonide, or fluticasone. Alternatively, or additionally, the other compound is a beta2 agonist such as salbutamol, terbutaline sulfate, formoterol, vilanterol, or salmeterol. Alternatively, or additionally, the other compound is a leukotriene receptor antagonist such as montelukast. Alternatively, or additionally, the other compound is a muscarinic antagonist such as ipratropium bromide. Alternatively, or additionally, the other compound is a theophylline such as aminophylline. Alternatively, or additionally, the other compound is magnesium sulfate. Alternatively, or additionally, the other compound is a mast cell stabilizer such as sodium cromoglycate or nedocromil. Alternatively, or additionally, the other compound is an anti-IL-5 antibody. In one example, the anti-IL-5 antibody is mepolizumab. Alternatively, or additionally, the other compound is an anti-IgE antibody. In one example, the anti-IgE antibody is omalizumab. Alternatively, or additionally, the other compound is an anti-1L-17A antibody. In one example, the anti-1L-17A antibody is secukinumab.

In one example, the compound that inhibits G-CSF signaling is administered simultaneously with the other compound. In one example, the compound that inhibits G-CSF signaling is administered before the other compound. In one example, the compound that inhibits G-CSF signaling is administered after the other compound.

In some examples, the compound that inhibits G-CSF signaling is administered in combination with a cell. In some examples, the cell is a stem cell, such as a mesenchymal stem cell.

In some examples, the compound that inhibits G-CSF signaling is administered in combination with a gene therapy.

Dosages and Timing of Administration

Suitable dosages of compounds of the present disclosure will vary depending on the specific compound and/or the subject being treated. It is within the ability of a skilled physician to determine a suitable dosage, e.g., by commencing with a sub-optimal dosage and incrementally modifying the dosage to determine an optimal or useful dosage. Alternatively, to determine an appropriate dosage for treatment, data from cell culture assays or animal models can are used, wherein a suitable dose is within a range of circulating concentrations that include the $ED_{50}$ of the active compound with little or no toxicity. The dosage may vary within this range depending upon the dosage form employed and the route of administration utilized. A therapeutically effective dose can be estimated initially from cell culture assays. A dose may be formulated in animal models to achieve a circulating plasma concentration range that includes the IC50 (i.e., the concentration of the compound which achieves a half-maximal inhibition of symptoms) as determined in cell culture. Such information can be used to more accurately determine useful doses in humans. Levels in plasma maybe measured, for example, by high performance liquid chromatography.

In some examples, the compound that inhibits G-CSF signaling is administered systemically. In some examples, the compound that inhibits G-CSF signaling is administered locally.

In some examples, a method of the present disclosure comprises administering a therapeutically effective amount of a compound described herein.

The term "therapeutically effective amount" is the quantity which, when administered, improves the prognosis and/or state of the subject and/or that reduces or inhibits one or more symptoms of asthma to a level that is below that observed and accepted as clinically diagnostic or clinically characteristic of that condition. Alternatively, a therapeutically effective amount is a quantity which, when administered prevents the occurrence or exacerbation of one or more symptoms of asthma. The amount to be administered will depend on the particular characteristics of the subtype of asthma to be treated, the type and stage of condition being treated, the mode of administration, and the characteristics of the subject, such as general health, other diseases, age, sex, genotype, and body weight. A person skilled in the art will be able to determine appropriate dosages depending on these and other factors. Accordingly, this term is not to be construed to limit the present disclosure to a specific quantity, e.g., weight or amount of compound, rather the present disclosure encompasses any amount of the compound that inhibits G-CSF signaling sufficient to achieve the stated result in a subject. In one example, a therapeutically effective amount of the compound that inhibits G-CSF signaling does not induce neutropenia.

In some examples, a method of the present disclosure comprises administering a prophylactically effective amount of a compound described herein. As used herein, the term "prophylactically effective amount" shall be taken to mean a sufficient quantity of a compound to prevent or inhibit or delay the onset of one or more detectable symptoms of asthma. The skilled artisan will be aware that such an amount will vary depending on, for example, the specific compound administered and/or the particular subject and/or the type or severity or level of condition and/or predisposition (genetic or otherwise) to the condition. Accordingly, this term is not to be construed to limit the present disclosure to a specific quantity, e.g., weight or amount of compound, rather the present disclosure encompasses any amount of the compound that inhibits G-CSF signaling sufficient to achieve the stated result in a subject. In one example, a prophylactically effective amount of the compound that inhibits G-CSF signaling does not induce neutropenia.

For in vivo administration of the compounds described herein, normal dosage amounts may vary from about 10ng/kg up to about 100 mg/kg of an individual's body weight or more per day. Exemplary dosages and ranges thereof are described herein.

For repeated administrations over several days or longer, depending on the severity of the disease or disorder to be treated, the treatment can be sustained until a desired suppression of symptoms is achieved.

In some examples, the compound that inhibits G-CSF signaling is administered at an initial (or loading) dose of between about 0.1 mg/kg to about 30 mg/kg, such as from about 1 mg/kg to about 10 mg/kg. The compound that inhibits G-CSF signaling can then be administered at a lower maintenance dose of between about 0.01 mg/kg to about 5 mg/kg, such as from about 0.05 mg/kg to about 1 mg/kg. The maintenance doses may be administered every 7-30 days, such as, every 10-15 days, for example, every 10 or 11 or 12 or 13 or 14 or 15 days. In this regard, a maintenance dose can be used in order to maintain a therapeutically effective level of the compound in the blood of the subject for a length of time.

In some examples, the compound that inhibits G-CSF signaling is administered at a dose of between about 0.01 mg/kg to about 50 mg/kg, such as between about 0.1 mg/kg to about 40 mg/kg, for example, between about 2 mg/kg to about 30 mg/kg, for example, between about 5 mg/kg to about 25 mg/kg.

In some examples, the compound that inhibits G-CSF signaling is administered at a dose of about 5 mg/kg. In some examples the compound that inhibits G-CSF signaling is administered at a dose of about 10 mg/kg. In some examples the compound that inhibits G-CSF signaling is administered at a dose of about 25 mg/kg.

In some examples, the compound that inhibits G-CSF signaling is administered without a higher loading dose or a lower maintenance dose.

In some examples, the compound that inhibits G-CSF signaling is administered as a single dose.

In some examples, numerous doses are administered, e.g., every 7-30 days, such as, every 10-22 days, for example, every 10-15 days, for example, every 10 or 11 or 12 or 13 or 14 or 15 or 16 or 17 or 18 or 19 or 20 or 21 or 22 days. For example, the compound that inhibits G-CSF signaling is administered every 7 days or every 14 days or every 21 days.

In some examples, at the time of commencing therapy, the subject is administered the compound that inhibits G-CSF signaling on no more than 7 consecutive days or 6 consecutive days or 5 consecutive days or 4 consecutive days.

In the case of a subject that is not adequately responding to treatment, multiple doses in a week may be administered. Alternatively, or in addition, increasing doses may be administered.

In another example, for subjects experiencing an adverse reaction, the initial (or loading) dose may be split over numerous days in one week or over numerous consecutive days.

Administration of a compound according to the methods of the present disclosure can be continuous or intermittent, depending, for example, on the recipient's physiological condition, whether the purpose of the administration is therapeutic or prophylactic, and other factors known to skilled practitioners. The administration of a compound may be essentially continuous over a preselected period of time or may be in a series of spaced doses, e.g., either during or after development of a condition.

Kits

Another example of the disclosure provides kits containing compounds useful for the treatment of asthma as described above.

In one example, the kit comprises (a) a container comprising a compound that inhibits G-CSF signaling as described herein, optionally in a pharmaceutically acceptable carrier or diluent; and (b) a package insert with instructions for reducing an effect of asthma in a subject.

In accordance with this example of the disclosure, the package insert is on or associated with the container. Suitable containers include, for example, bottles, vials, syringes, etc. The containers may be formed from a variety of materials such as glass or plastic. The container holds or contains a composition that is effective for treating the asthma and may have a sterile access port (for example, the container may be an intravenous solution bag or a vial having a stopper pierceable by a hypodermic injection needle). At least one active agent in the composition is the compound that inhibits G-CSF signaling that inhibits G-CSF signaling. The label or package insert indicates that the composition is used for treating a subject eligible for treatment, e.g., one having or predisposed to asthma, with specific guidance regarding dosing amounts and intervals of compound and any other medicament being provided. The kit may further comprise an additional container comprising a pharmaceutically acceptable diluent buffer, such as bacteriostatic water for injection (BWFI), phosphate-buffered saline, Ringer's solution, and/or dextrose solution. The kit may further include other materials desirable from a commercial and user standpoint, including other buffers, diluents, filters, needles, and syringes.

The present disclosure includes the following non-limiting Examples.

EXAMPLES

Example 1

Materials and methods

Animal Model of Asthma with Neonatal Co-Infection and House Dust Mite Sensitisation Advanced pregnant BALB/c dams (Animal Resources Centre, Western Australia) were housed separately and monitored for birth with minimal disruption. Upon birth, dams were housed with their litters until weaning at 3 weeks of age. Mice were housed at 22° C. under normal 12 h:12 h light:dark cycle, and given free access to a normal diet and water. Female pups (litter sizes between 5 and 7 pups) were used for the experimental protocol. Neonatal mice were infected with *S. pneumoniae* and/or influenza A virus (IAV) as previously described in FitzPatrick et al., Sci Rep, (2016) 6:22751, with the following minor modifications. At 8 days of age, BALB/c infant mice were inoculated intranasally without anaesthesia with *S. pneumoniae* (serotype 19F strain EF3030, $2 \times 10^3$ CFU) in a volume of 3 µl sterile saline or saline alone (SAL). At 15 days of age, mice were inoculated by the intranasal route with IAV (strain HKx31, H3N2, 500 PFU) in a volume of 3 µl sterile saline or vehicle. House dust mite (HDM) extract (*Dermatophagoides pteronyssinus*) was obtained from Greer Laboratories (Charlotte, NC, USA). At 20—21 days of age, weaned female mice were sensitized intranasally with HDM aeroallergen (10 µg in 10 µL saline) or vehicle (10 µL saline alone, VEH) under isoflurane anaesthesia for 5 consecutive days per week over 3 weeks. All outcomes were assessed 24 h following the final HDM treatment (or VEH) when mice were approximately 6 weeks of age. In a separate experiment, 100 μg of anti-granulocyte colony stimulating factor receptor (VR81) antibody or isotype control (ISO) antibody (BM4; CSL Limited, Parkville, Victoria, Australia) was administered to co-infected/HDM-exposed mice via i.p. injection every second day during the last week of HDM sensitisation. Uninfected mice that only received VEH during the HDM exposure were used as control (SAL). All outcomes were assessed 24 h following the final HDM/antibody treatment when mice were approximately 6 weeks of age.

Antibodies

VR81 is a mouse monoclonal IgG1κ antibody produced against the extracellular domain of murine G-CSFR and blocks G-CSF binding to G-CSFR as described (Campbell et al. *Journal of Immunology*, 197(11) (2016) 4392-4402). In this regard, VR81 is a mouse surrogate antibody for C1.2 and C1.2G described herein and in WO2012171057. BM4 is an monoclonal mouse isotype IgG1κ control antibody.

Lung Function

In vivo airway reactivity was measured using a small animal computer-controlled piston ventilator (Flexivent, SCIREQ® Montreal, QC, Canada) as previously described (FitzPatrick et al., Sci Rep, 2016 6:22751). Briefly, mice were anaesthetised with ketamine (125 mg/kg) and xylazine (25 mg/kg) before tracheotomy was performed and a cannula was inserted. In vivo airway responsiveness was assessed in response to nebulized PBS and increasing doses of methacholine (MCh, 10 mg/mL, 30 mg/mL and 100 mg/mL).

Tissue Collection and Quantification of *S. pneumoniae*

Bronchoalveolar lavage (BAL) was performed and total and differential BAL cell counts determined as previously described (Anthony et al., Am J Respir Crit Care Med, 2013. 188:179-86). Nasopharyngeal tissue was collected and homogenised. Serial dilutions of BAL fluid and nasopharyngeal tissue homogenates were cultured on horse blood agar plates with gentamycin (5 μg/mL) to determine *S. pneumoniae* load as previously described (FitzPatrick et al., Sci Rep, 2016 6:22751). A real time quantitative PCR method was used to measure *S. pneumoniae* in lung tissue using commercial qPCR kit from Qiagen. Briefly, bacterial DNA was isolated by homogenising lung tissue in Trizol using TissueLyser (Qiagen) in accordance to the manufacturer's instructions (Life Technologies). *S. pneumoniae* DNA qPCR was performed via a two-step PCR cycle as per manufacturer's instructions (Qiagen) using standard curve generated from a known quantity of pneumococci.

Flow Cytometric Assessment of Immune Cells in Lung

All anti-mouse antibodies were purchased from BD Biosciences, namely FITC-conjugated CD45, PE-conjugated Siglec F, APC/Cy7-conjugated Ly6G, PB-conjugated CD4, BV605-conjugated IL-4. Single cell suspension preparation from fresh lungs and flow cytometric analysis on cell surface markers (CD45, Ly6G, Siglec F, and CD4) were performed as previously described (Wang et al., Clin Sci (Lond), 2017. 131:2347-2362). A strict gating strategy was used to determine different immune cell populations and propidium iodide (Life Technologies) was used to exclude dead cells. Cell singlets were gated using FSC-H vs FSC-W and SSC-H vs SSC-W. Neutrophils were gated as intermediate or high FSC-A and SSC-A, which displayed these cells as distinct clusters compared to lymphocytes and myeloid cells. In addition, neutrophils were classified as $CD45^{Hi}$, Siglec F$^-$, and Ly6G$^+$. T cells were gated as intermediate or low FSC-A and SSC-A, as well as high expression of CD45 and CD4. For IL-4 staining, isolated cells were firstly cultured and stimulated for 2 h using a T cell stimulation cocktail (Life Technologies) before staining. All cells were permeabilized and fixed using a Cell Fixation & Cell Permeabilization Kit (Life Technologies) before being analysed on a BD FACSARIA III flow cytometer. Data were then analyzed with FlowJo v7.6.5 (Tree Star, Ashland, OR).

Histology and Immunohistochemistry

The left lobe of lung was removed post mortem and immediately fixed in 10% w/v neutral-buffered formalin. Tissues were paraffin-embedded and cut at a thickness of 4 μm. Sections were stained with hematoxylin and eosin (H&E), masson trichrome (MT) for assessment of epithelial and sub-epithelial collagen content or with Alcian blue-periodic acid Schiff (AB-PAS) for assessment of goblet cell transdifferentiation. To assess the presence of airway smooth muscle bulk, primary antibody to anti-α smooth muscle actin (α-SMA, Dako, Glostrup, Denmark) was used. Whole lung sections were scanned using a slide scanner (Olympus VS-120) and morphometric analysis was performed using CellSens Dimensions software from Olympus. Morphometric evaluation of lung tissue sections was analysed on a minimum of four bronchi per mouse section selected according to size (100 to 350 μm luminal diameter). Briefly, a 30 μm band was selected around the subepithelial layer of randomly selected bronchioles per section and the percent positive stain areas analysed from α-SMA, AB-PAS and MT stained slides using standardised threshold values. Airway inflammation in H&E sections was graded blinded as an average of the entire lung section score with the average scores of five individual airways as previously described (Coomes et al., Mucosal Immunol, 2016). For entire lung section; presence of perivascular inflammation=1, inflammation around 3 or more bronchioles=2, dense inflammatory foci 3 cells deep=3 and loss of lung architecture=4. For each individual airway: presence of inflammation=1; 50% inflammation around bronchiole=2; 100% inflammation around bronchiole=3; and dense inflammation bridging two bronchioles=4.

Reverse Transcriptase Quantitative Real-Time PCR (RT-qPCR) for Gene Expression Analysis RNA was purified from snap-frozen lung tissue using RNeasy kit as per manufacturer's instructions and cDNA was prepared as previously described (Bozinovski et al., Am J Respir Cell Mol Biol, 2011. 45:229-36). RT-qPCR was performed using bioinformatically validated Taqman primer/probes. All threshold cycle values (Ct) were normalized to a reference gene (glyceraldehyde phosphate dehydrogenase; GAPDH) and the relative fold change determined by the ΔΔCt method as previously described (Bozinovski et al., Am J Respir Cell Mol Biol, 2011. 45:229-36).

Measurement of EF3030- and HDM-Specific IgG Response

The whole-cell ELISA method for determining EF3030-specific IgG levels in serum was based on a previously published method (Cohen et al., PLoS One, 2011 6: e25558). The pneumococcal EF3030 strain was grown to late-log phase at OD580 nm 1.0, washed and resuspended in PBS to an OD580 nm of 1.0 and coated at 100 μl/well onto 96-well high-binding Nunc Maxisorp plates (Thermo Fisher Scientific, MA, USA) and incubated overnight at 4° C. Plates were washed with PBS-Tween (0.05%) and blocked with PBS-10% FCS for 1 h at 37° C. After washing, serum samples were added to the plate in the range between neat to 1:100 and incubated for 1 h at 37° C. Plates were washed and developed with a biotinylated goat anti-mouse IgG for 1 h at 37° C. followed by streptavidin-HRP (both 1:500; Sigma-Aldrich, St Louis, USA) for a further 1 h at 37° C. The reaction was then developed with TMB substrate solution for 7 min and stopped with the addition of $H_3PO_4$. Optical densities were measured in a microplate reader (Biotek, VT, USA) at an absorbance of 450 nm (reference 630 nm). For HDM-specific IgG ELISA, 96-well Maxisorp plates were coated with HDM at 4 µg/mL in carbonate-bicarbonate buffer pH 9.6 overnight at 4° C. A similar method to the one described above for EF3030 IgG was then used to determine levels of anti-HDM IgG in serum.

Peroxidase Assay

Peroxidases from neutrophils and eosinophils were extracted by homogenising ground lung tissue (20 mg) in 0.4 mL extraction buffer (50 mM potassium phosphate monobasic pH 6.0, 0.5% w/v hexa-decyl-trimethyl ammonium bromide and 10 mM EDTA). Following centrifugation, 10 µl lung lysate was incubated with 90 µl reaction buffer (50 mM potassium phosphate pH 6.0, 0.167 mg/mL o-Dianisidine [Fast Blue B, Sigma] and 0.005% $H_2O_2$). The change in absorbance ($A_{460}$) (between 2 min and 3 min post incubation) resulted from the peroxidase-mediated decomposition of $H_2O_2$ and oxidation of o-Dianisidine was measured using a Clariostar plate reader.

Neutrophil Elastase and Double Stranded DNA (dsDNA) Measurement

Neutrophil elastase activity was measured on BAL fluid with an EnzChek™ Elastase Assay Kit according to manufacturer's instructions. Content of double stranded DNA (dsDNA) in the BAL fluid was also measured using Quant-iT PicoGreen dsDNA reagent (Life Technologies), according to the manufacturer's instructions.

Data Analysis

Data are presented as the mean±standard error of mean (SEM). All data were statistically analysed using GraphPad Prism 5.0 (Graphpad, San Diego, CA). Where detailed and appropriate, one-way analyses of variance (ANOVA) with Dunnett's or Bonferroni's post-hoc tests were used. For bacterial load data, the non-parametric Kruskall-Wallis with Dunn's post-test was performed. $p<0.05$ was considered to be statistically significant.

Example 2

Asthma Model

A previously published infection model of neonatal inoculation with S. pneumoniae and IAV (Diavatopoulos et al., Faseb J, 2010. 24:1789-98) was superimposed with subsequent repeated HDM aeroallergen exposure to generate a mouse model of asthma (FIG. 1).

Figure 2:
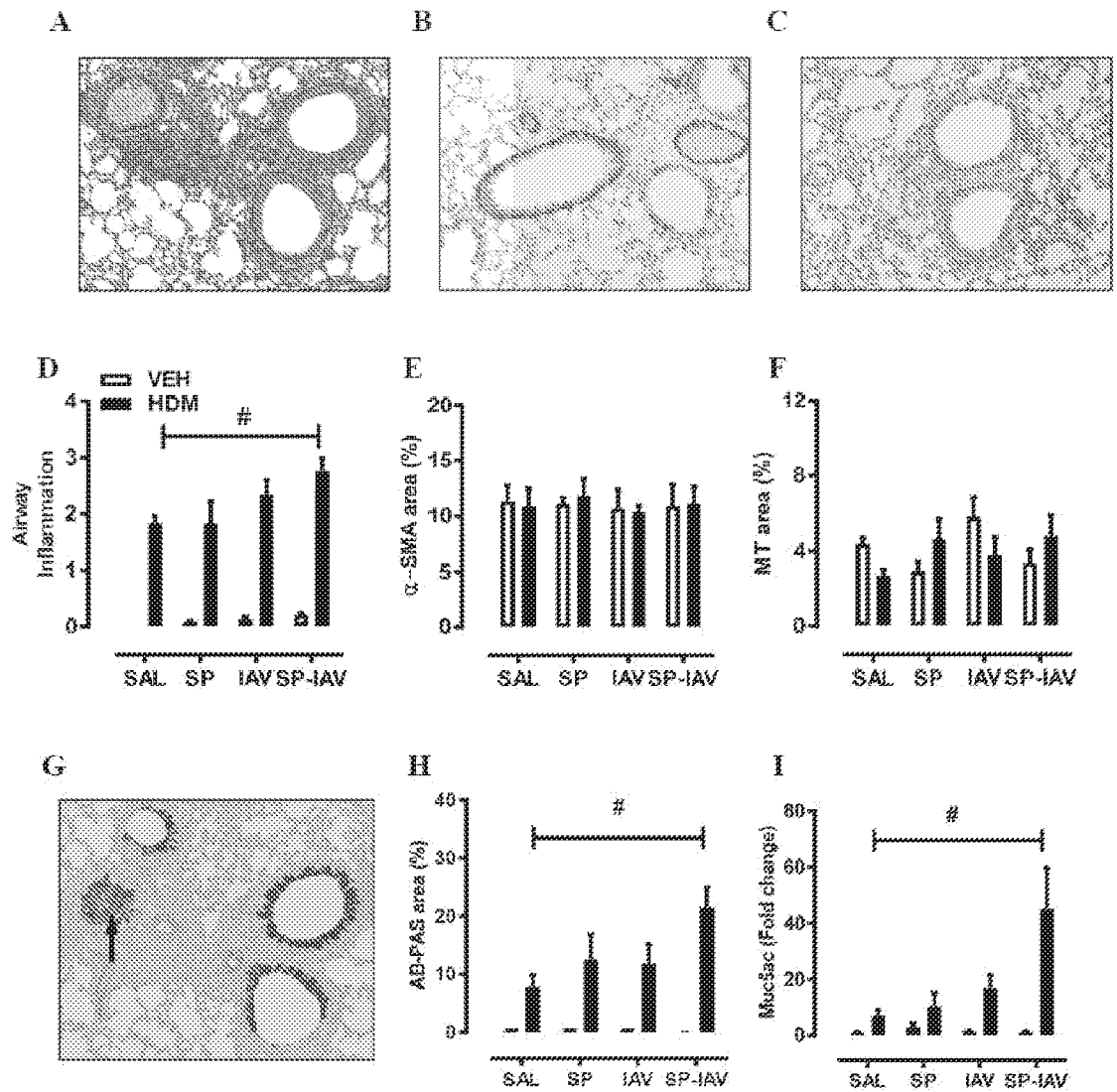
FIG. 2 illustrates airway inflammation and airway remodeling induced by HDM sensitization in the asthma model. Representative images (100× optical zoom) of SP-IAV/HDM lung sections stained with (A) haemotoxylin and Eosin (H&E) to assess tissue and bronchiole inflammation, (B) anti-α-smooth muscle actin immunostaining to assess smooth muscle bulk around bronchioles, and (C) Masson's Trichrome stain to assess collagen deposition around airways. (D-F) The corresponding quantifications for each stain are presented. (G) Alcian blue-periodic acid Schiff/AB-PAS was used to stain for mucus and (H) degree of mucus staining in surrounding airways were quantified as detailed in Example 1. Black arrow in (G) indicates a complete airway obstruction by mucous plugging. (I) Expression of mucin gene Muc5ac in lung tissue was analyzed by RT-qPCR. n=4-8 per group; #p<0.05, one way ANOVA with Bonferroni's post-hoc test compared to SAL/VEH. Error bars represent mean±SEM.

Histological assessment of lung inflammation in H&E stained lung sections demonstrated significant pathology in mice exposed to co-infection and HDM (representative images presented in FIG. 2A). Scoring of the degree of airway inflammation revealed that HDM was the predominant cause of pathology and this was significantly increased by neonatal co-infection (FIG. 2D). Airway remodelling processes, including smooth muscle hypertrophy, collagen deposition and mucous plugging were also assessed histologically. Quantification of α-smooth muscle actin areas surrounding the bronchioles (FIG. 2B) revealed no significant differences across treatment groups (FIG. 2E). Similar analysis on collagen areas from Masson's trichrome (MT) stain (FIG. 2C) also showed no statistical significance (FIG. 2F). Notably, an expansion of mucus-producing goblet cells as demonstrated by Alcian blue-periodic acid Schiff (AB-PAS) positive areas (FIG. 2G) was observed with repeated HDM challenge (FIG. 2H). This expansion was not altered by inoculation with a single respiratory pathogen; however co-infection with S. pneumoniae and IAV significantly increased goblet cells/mucus areas surrounding the bronchioles (FIG. 2H, $p<0.05$ vs SAL/HDM). Complete airway obstruction by a mucus plug was also evident in the bronchiole of co-infected mice with HDM exposure (FIG. 2G, black arrow). This finding was in accordance with expression of mucin gene encoding Muc5ac, which was only significantly increased in co-infected neonatal mice chronically challenged with repeated HDM exposure relative to SAL/HDM (FIG. 2I).

Figure 3:
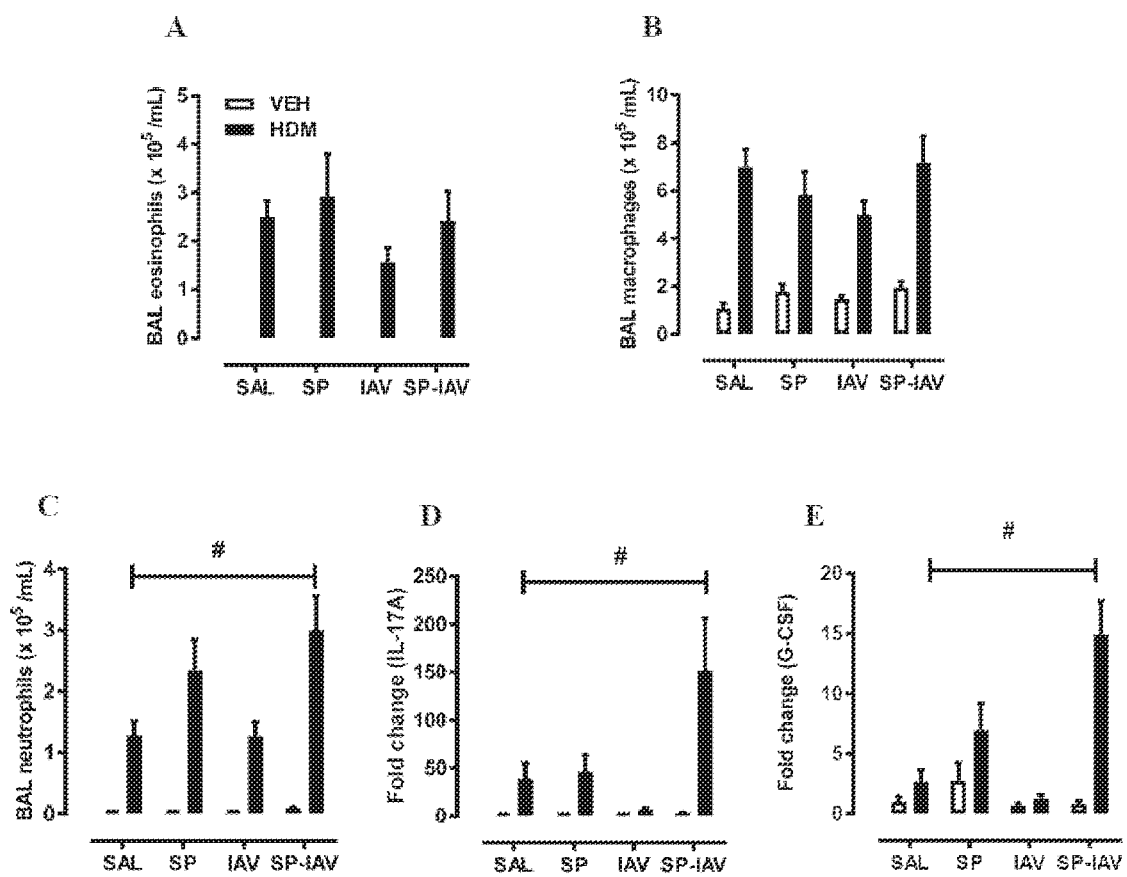
FIG. 3 shows that neonatal co-infection worsens neutrophilic inflammation but not eosinophilic responses driven by HDM challenge. Total cells from bronchoalveolar lavage (BAL) were counted and cytospins were prepared for the assessment of (A) eosinophil, (B) macrophage and (C) neutrophil numbers. RT-qPCR was performed on lung tissue for assessment of expression of genes that regulate neutrophil mobilisation including (D) IL-17A and (E) granulocyte-colony stimulating factor (G-CSF) using GAPDH as a reference gene. Results were expressed as fold change relative to SAL/VEH group. n=4-8 per group; #p<0.05, one way ANOVA with Bonferroni's post-hoc test compared to SAL/VEH. Error bars represent mean±SEM.

The number of BAL eosinophil and macrophages were elevated by HDM challenge but were not significantly altered by neonatal infection (FIG. 3A, B). BAL neutrophil counts were also elevated by HDM challenge (FIG. 3C) and this was further exacerbated by neonatal co-infection ($p<0.05$, vs. SAL/HDM). To assess molecular drivers of neutrophilic inflammation in this model, two key mediators that promote neutrophil mobilisation, IL-17A and G-CSF, were assessed by RT-qPCR. HDM alone increased expression of IL-17A and G-CSF and this effect was markedly increased in mice that were co-infected as neonates (FIG. 3D, E).

Example 3

Effect of Inhibiting G-CSF Signaling on Immune Cells and Inflammation

Figure 4:
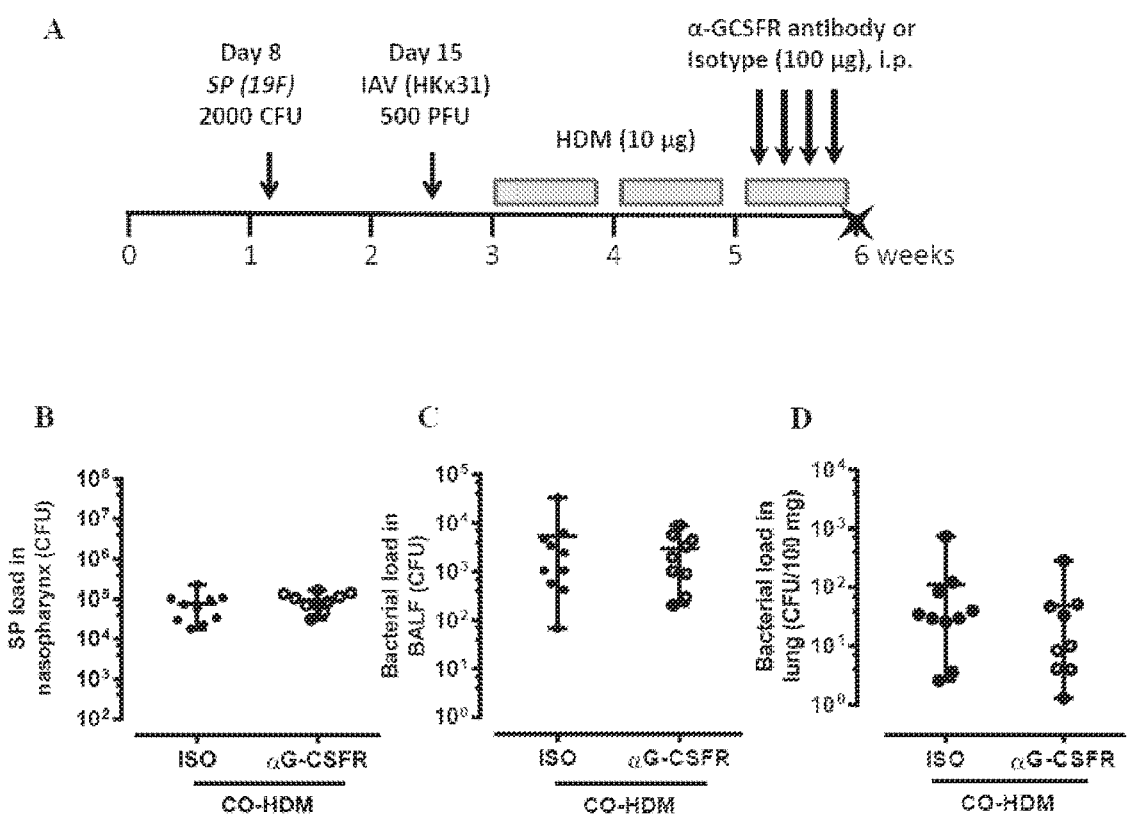
FIG. 4 shows the effect of inhibiting G-CSF signaling on bacterial load in the airways. In the last week of HDM treatment, mice co-infected with SP and IAV were injected intraperitoneally with 100 μg anti-G-CSFR antibody (α-G-CSFR) or isotype control antibody (ISO) every second day (A). Twenty-four hours after final HDM/antibody administration, S. pneumoniae load in the nasopharynx (B), bronchoalveolar lavage (BAL) fluid (C) and lung tissue (D) was determined (n=9-10 per group). Error bars represent mean±range.

To investigate the significance of the G-CSF/G-CSFR pathway in asthma, G-CSFR was neutralised by administering an anti-G-CSFR monoclonal antibody (VR81, 100 µg) every second day during the last week of HDM challenge (FIG. 4A).

The load of S. pneumoniae in the nasopharynx 24 h after the last VR81/HDM treatment was not significantly different following VR81 administration when compared to isotype control-treated (ISO) mice (FIG. 4B). S. pneumoniae load in the BALF (FIG. 4C) or lung tissue (FIG. 4D) was also not significantly altered by anti-G-CSFR treatment.

Figure 5:
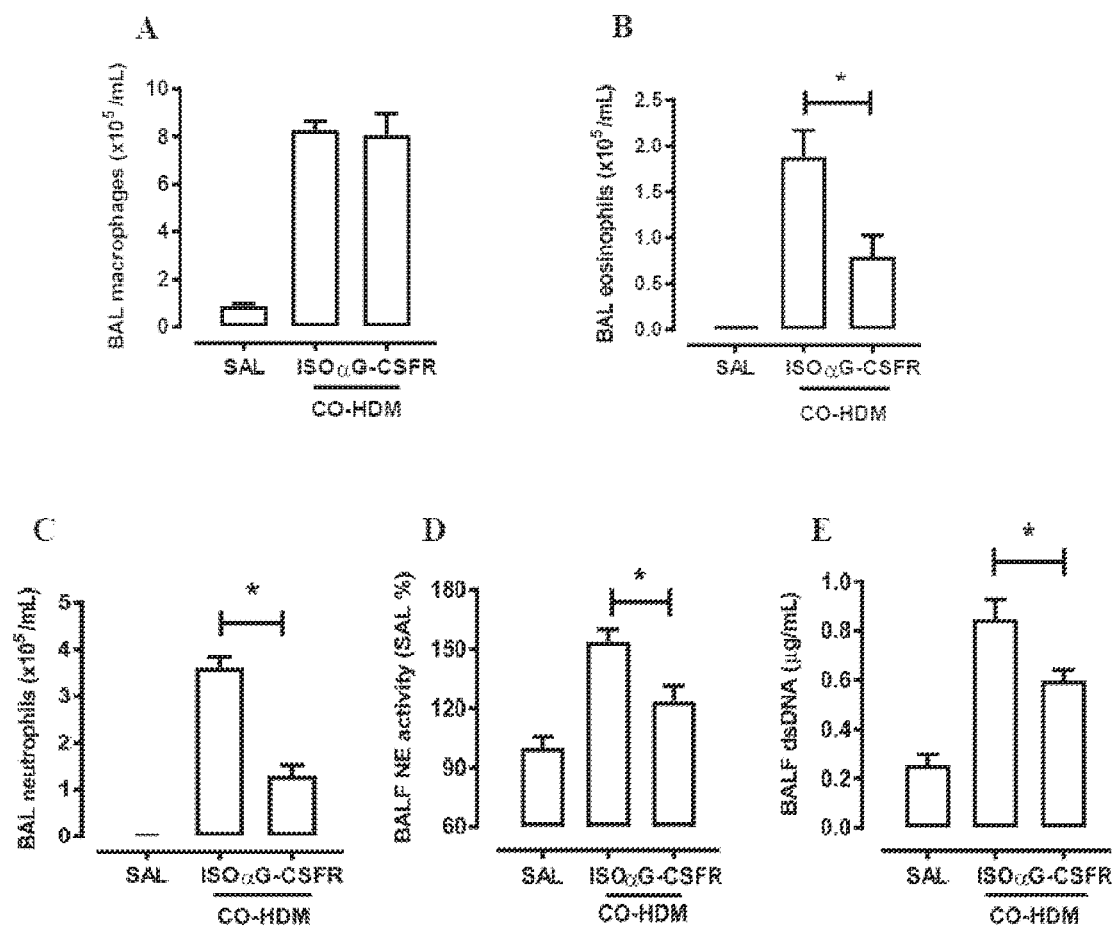
FIG. 5 shows the effect of inhibiting G-CSF signaling on immune cell levels and inflammation in bronchoalveolar lavage (BAL) fluid. Total cells from bronchoalveolar lavage (BAL) fluid were counted and cytospins were prepared for the assessment of (A) macrophage, (B) eosinophil and (C) neutrophil numbers in co-infected/HDM-exposed mice (CO-HDM) following treatment with anti-G-CSFR antibody (α-G-CSFR) or isotype control antibody (ISO). Naive mice that only received saline during infection and HDM exposure were used as control (SAL). Neutrophil elastase (NE) activity (D) and double stranded DNA (dsDNA) content in BALF (E) were measured as markers for NETosis. n=10 per group; *p<0.05, one way ANOVA with Dunnett's post-hoc test compared to CO-HDM/ISO. Error bars represent mean±SEM.

The VR81 administration did not alter macrophage numbers in the BALF (FIG. 5A), but effectively reduced eosinophil and neutrophil numbers (FIG. 5B and C, by 58% and 64% respectively, both $p<0.05$ vs ISO). The neutralising G-CSFR antibody, VR81, significantly reduced NETosis markers, including neutrophil elastase (NE) and double stranded DNA (dsDNA), in BALF of the co-infected mice exposed to repeated HDM challenge compared to isotype control-treated animals (FIG. 5D, E).

Figure 6:
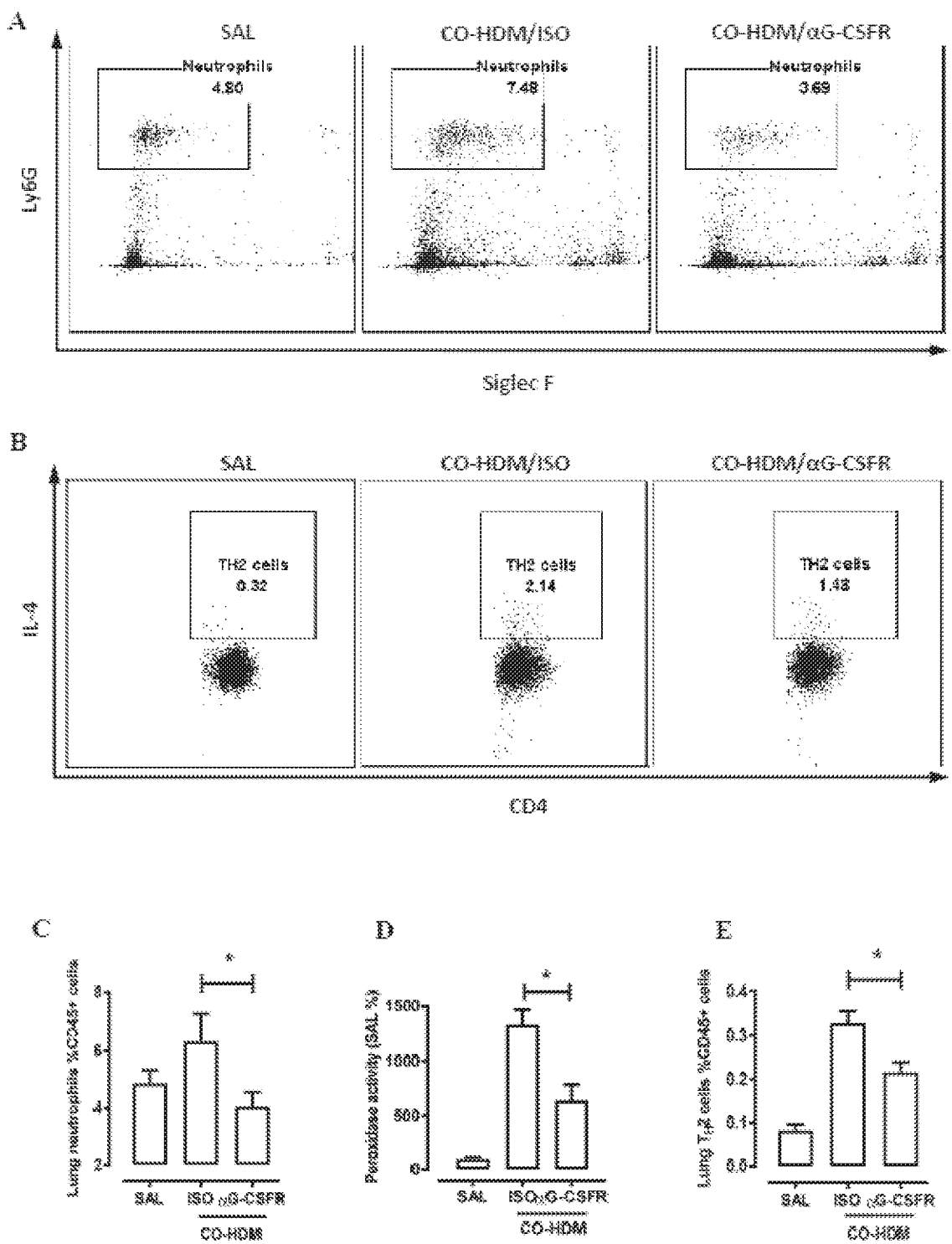
FIG. 6 shows the effect of inhibiting G-CSF signaling on immune cell levels and peroxidase activity in the lungs. Lung immune cells were prepared from co-infected/HDM-exposed mice (CO-HDM) following treatment with anti-G-CSFR antibody (α-G-CSFR) or isotype control antibody (ISO). Naive mice that only received saline during infection and HDM exposure were used as control (SAL). Neutrophils were gated (Siglec F$^-$, Ly6G$^+$) with representative dot plots (A) and presented as percentage of total immune cells (CD45$^+$ cells) (C). T$_H$2 cells were gated (CD4$^+$, IL-4$^+$) with representative dot plots (B) and presented as percentage of total immune cells (CD45$^+$ cells) (E). Peroxidase activity from lung tissue was determined and presented as a percentage of the SAL control group (D). n=10 per group; *p<0.05, one way ANOVA with Dunnett's post-hoc test compared to CO-HDM/ISO. Error bars represent mean±SEM.

Assessment of lung inflammation by flow cytometry demonstrated the percentage of neutrophils (Ly6G$^+$, Siglec F$^-$) relative to the total CD45$^+$ immune cell population significantly increased in CO-HDM/ISO mice, which was markedly inhibited by VR81 treatment (FIG. 6C). The degree of lung neutrophilic inflammation was in accordance with peroxidase activity, which was increased by 13-fold in CO-HDM/ISO and reduced by 50% in VR81 treated mice (FIG. 6D, $p<0.05$). A similar trend was also observed for $T_H2$ cells (CD45$^+$, CD4$^+$, IL-4$^+$), where CO-HDM/ISO mice displayed a 3-fold increase compared to naive mice and α-G-CSFR treatment reduced the proportion of $T_H2$ cells by approximately 50%.

Example 4

Effect of Inhibiting G-CSF Signaling on Mucus Production and Lung Function

Figure 7:
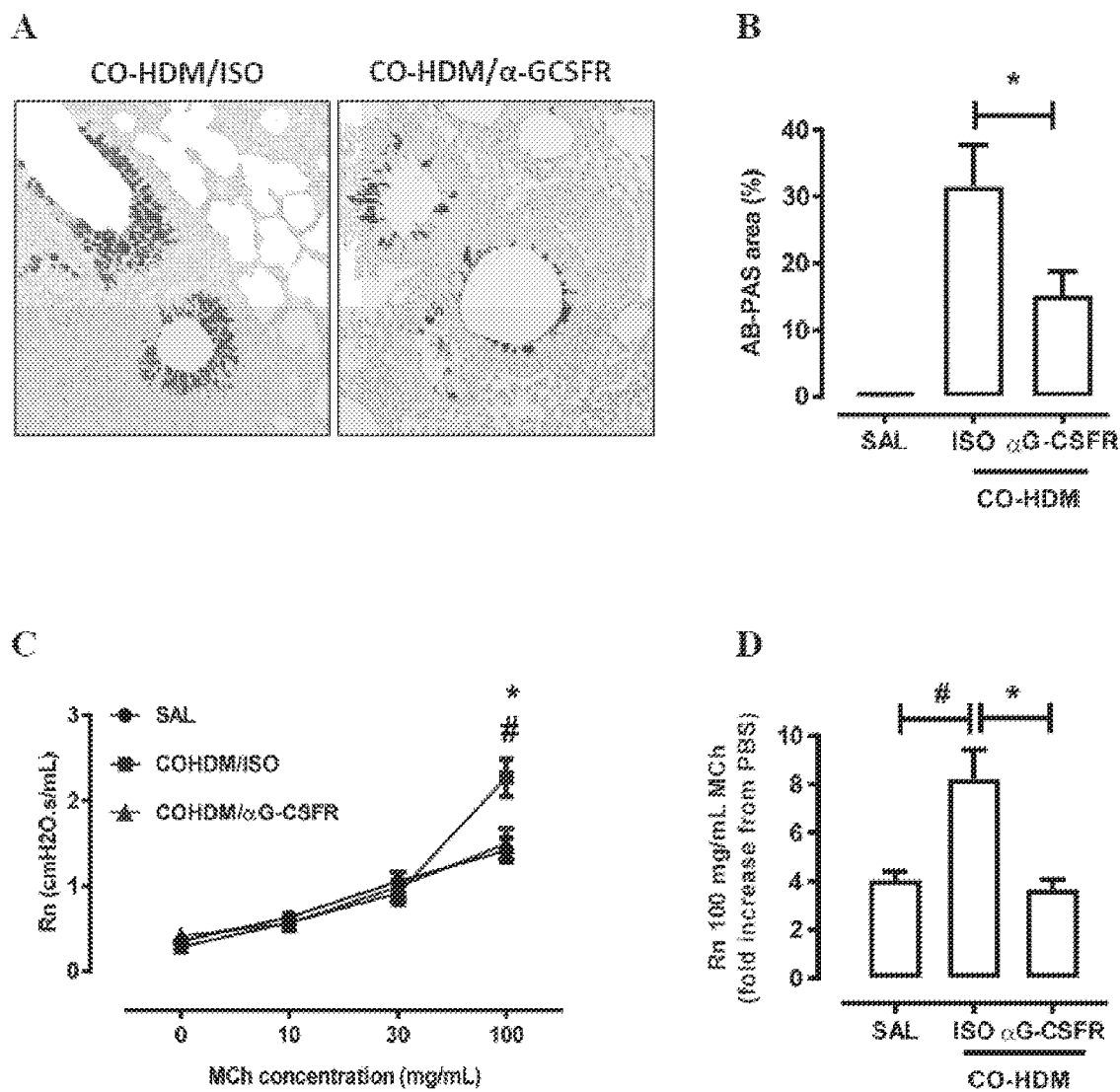
FIG. 7 shows the effect of inhibiting G-CSF signaling on mucus production and airway hyper-responsiveness. Representative images (100× optical zoom) of SP-IAV/HDM lung sections show (A) increased mucus staining (Alcian Blue-Periodic Acid Schiff/AB-PAS stain) in response to co-infection and HDM challenge (CO-HDM) that was significantly reduced by treatment with α-G-CSFR antibodies (B). Newtonian resistance (Rn, central airway resistance) was measured in vivo using Flexivent in response to nebulized PBS and increasing doses of methacholine (MCh, 10 mg/mL, 30 mg/mL and 100 mg/mL) (C). Rn at the maximum methacholine dose of 100 mg/mL was also presented (D). *p<0.05, one way ANOVA with Dunnett's post-hoc test shows CO-HDM/ISO is significantly increased compared CO-HDM/α-G-CSFR; #p<0.05, one way ANOVA with Dunnett's post-hoc test shows CO-HDM/ISO is significantly increased compared to SAL control. Error bars represent mean±SEM.

The effect of anti-G-CSFR antibody (VR81) treatment on goblet cell proliferation in lung sections was assessed (FIG. 7A; representative AB-PAS stain images in ISO and VR81 treated mice). Elevated mucus production observed in isotype control treated mice was significantly reduced by VR81 treatment by approximately 50% (FIG. 7B, $p<0.05$ vs CO-HDM/ISO).

To determine whether mucus over-production induced airway hyper-responsiveness (AHR), lung mechanical function was measured in response increasing doses of nebulized methacholine (MCh, 10 mg/mL, 30 mg/mL and 100 mg/mL). Newtonian resistance (Rn, which is equivalent to central airway resistance) increased in a dose-dependent manner irrespective of the treatment group, with only CO-HDM/ISO showing a further significant increase at 100 mg/mL (FIG. 7C, $p<0.05$ vs. SAL). At this maximum Mch dose, AHR was observed in mice from CO-HDM/ISO group, eliciting an 8-fold increase in Rn from PBS compared to a 4-fold increase in naive mice (FIG. 7D, $p<0.05$ vs SAL). Anti-G-CSFR antibody (VR81) therapy completely restored the lung function and abolished AHR in co-infection/HDM treated mice (FIG. 7D, $p<0.05$ vs CO-HDM/ISO).

---

The invention claimed is:

1. A method for treating asthma in a subject, the method comprising administering an antibody that binds to granulocyte colony stimulating factor receptor (G-CSFR) and inhibits granulocyte colony stimulating factor (G-CSF) signaling, wherein the antibody comprises:
   (a) a heavy chain variable region (VH) comprising three CDRs of a VH comprising an amino acid sequence set forth in SEQ ID NO: 4 and a light chain variable region (VL) comprising three CDRs of a VL comprising an amino acid sequence set forth in SEQ ID NO: 5; or
   (b) a VH comprising three CDRs of a VH comprising an amino acid sequence set forth in SEQ ID NO: 2 and a VL comprising three CDRs of a VL comprising an amino acid sequence set forth in SEQ ID NO: 3.

2. The method of claim 1, wherein the asthma is allergic asthma.

3. The method of claim 1, wherein the asthma is neutrophilic asthma.

4. The method of claim 1, wherein the asthma is severe asthma.

5. The method of claim 1, wherein the subject has airway bacterial colonisation and/or a respiratory viral infection.

6. The method of claim 1, wherein the antibody is administered in an amount sufficient to prevent or reduce the severity of an asthma exacerbation.

7. The method of claim 1, wherein the antibody is administered in an amount sufficient to reduce or prevent neutrophilic lung inflammation.

8. The method of claim 1, wherein the antibody is administered in an amount sufficient to reduce or prevent airway hyper-responsiveness (AHR).

9. The method of claim 1, wherein the compound that inhibits G-CSF signaling is administered in an amount sufficient to reduce or prevent an increase in mucus production.

10. The method of claim 1, wherein the antibody is administered in an amount sufficient to have one or more of the following effects in the subject's lung:
    (i) Reduce or prevent an increase in neutrophil levels;
    (ii) reduce or prevent an increase in neutrophil elastase levels;
    (iii) reduce or prevent an increase in extracellular double stranded DNA levels;
    (iv) reduce or prevent an increase in eosinophil levels; and
    (v) reduce or prevent an increase in $T_H2$ cell levels.

11. The method of claim 1, wherein the antibody comprises a VH comprising an amino acid sequence set forth in SEQ ID NO: 4 and a VL comprising an amino acid sequence set forth in SEQ ID NO: 5.

12. The method of claim 1, wherein the antibody comprises a VH comprising an amino acid sequence set forth in SEQ ID NO: 2 and a VL comprising an amino acid sequence set forth in SEQ ID NO: 3.

13. The method of claim 1, wherein the antibody comprises:
    (i) a heavy chain comprising an amino acid sequence set forth in SEQ ID NO: 14 or 18 and a light chain comprising an amino acid sequence set forth in SEQ ID NO: 15; or
    (ii) one heavy chain comprising an amino acid sequence set forth in SEQ ID NO: 14 and one heavy chain comprising an amino acid sequence set forth in SEQ ID NO: 18 and two light chains comprising an amino acid sequence set forth in SEQ ID NO: 15.

14. A method for treating asthma in a subject, the method comprising administering an antibody which comprises a heavy chain comprising an amino acid sequence set forth in SEQ ID NO: 14 or 18 and a light chain comprising an amino acid sequence set forth in SEQ ID NO: 15.

15. The method of claim 14, wherein the subject is human.

16. The method of claim 15, wherein the asthma is severe.

* * * * *